US012724024B2

(12) United States Patent
Qi et al.

(10) Patent No.: US 12,724,024 B2
(45) Date of Patent: Sep. 1, 2026

(54) SAMPLE ANALYZING SYSTEM, METHOD AND CELL IMAGE ANALYZING DEVICE

(71) Applicant: Shenzhen Mindray Bio-Medical Electronics Co., Ltd., Shenzhen (CN)

(72) Inventors: Huan Qi, Shenzhen (CN); Chaoyang Li, Shenzhen (CN); Yi Ye, Shenzhen (CN); Bo Ye, Shenzhen (CN); Shan Yu, Shenzhen (CN); Jin Li, Shenzhen (CN); Xuerong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1071 days.

(21) Appl. No.: 17/853,688

(22) Filed: Jun. 29, 2022

(65) Prior Publication Data

US 2022/0334100 A1 Oct. 20, 2022

Related U.S. Application Data

(63) Continuation of application No. PCT/CN2019/130608, filed on Dec. 31, 2019.

(51) Int. Cl.
*G01N 33/49* (2006.01)
*G01N 1/30* (2006.01)
(Continued)

(52) U.S. Cl.
CPC ............... *G01N 33/49* (2013.01); *G01N 1/30* (2013.01); *G01N 1/312* (2013.01); (Continued)

(58) Field of Classification Search
CPC .......... G01N 33/49; G01N 1/30; G01N 1/312; G01N 15/1431; G01N 35/00029; (Continued)

(56) References Cited

U.S. PATENT DOCUMENTS

| | | |
|---|---|---|
| 3,973,725 A | 8/1976 | Watanabe et al. |
| 2002/0154798 A1 | 10/2002 | Cong et al. |

(Continued)

FOREIGN PATENT DOCUMENTS

| | | |
|---|---|---|
| CN | 101407759 A | 4/2009 |
| CN | 103430077 A | 12/2013 |

(Continued)

OTHER PUBLICATIONS

Supplementary European Search Report in the European application No. 19958493.9, mailed on Dec. 12, 2022. 10 pages.

(Continued)

*Primary Examiner* — Charles Capozzi
*Assistant Examiner* — Alex Ramirez
(74) *Attorney, Agent, or Firm* — Syncoda LLC; Feng Ma

(57) ABSTRACT

A sample analysis system, method and a cell image analysis device. The sample analysis system includes a blood cell analyzer, a smear preparation apparatus, a cell image analysis apparatus, and a controller. The controller obtains a test result of at least one sample from the blood cell analyzer. When one sample needs to be analyzed by the cell image analysis device, the controller can further control an imaging condition used by the cell image analysis device according to a value of at least one type of cells in the test result of the sample, such that the cell image analysis device can automatically selects an imaging condition matching the test result for imaging according to different test results of the sample. Therefore, a matching imaging condition is used to specifically capture and analyze cell images of a smear of the sample, thereby improving processing efficiency and accuracy.

16 Claims, 13 Drawing Sheets

(51) Int. Cl.
*G01N 1/31* (2006.01)
*G01N 15/1429* (2024.01)
*G01N 35/00* (2006.01)
*G01N 35/10* (2006.01)

(52) U.S. Cl.
CPC ... *G01N 15/1431* (2013.01); *G01N 35/00029* (2013.01); *G01N 35/00732* (2013.01); *G01N 35/1002* (2013.01); *G01N 2035/00039* (2013.01); *G01N 2035/00138* (2013.01); *G01N 2035/00752* (2013.01)

(58) Field of Classification Search
CPC ......... G01N 35/00732; G01N 35/1002; G01N 2035/00039; G01N 2035/00138; G01N 2035/00752
See application file for complete search history.

(56) References Cited

U.S. PATENT DOCUMENTS

| | | | | |
|---|---|---|---|---|
| 2007/0076190 | A1* | 4/2007 | Nakaya | G01N 15/147 382/134 |
| 2010/0080440 | A1 | 4/2010 | Yamada | |
| 2012/0183198 | A1* | 7/2012 | Zahniser | G06V 20/693 382/133 |
| 2018/0314876 | A1 | 11/2018 | Rubin et al. | |

FOREIGN PATENT DOCUMENTS

| | | | |
|---|---|---|---|
| CN | 105136795 | A | 12/2015 |
| CN | 107478818 | A | 12/2017 |
| CN | 108844906 | A | 11/2018 |
| CN | 110383037 | A | 10/2019 |
| JP | 2007093356 | A | 4/2007 |
| JP | 2007093470 | A | 4/2007 |
| WO | 2019198094 | A1 | 10/2019 |

OTHER PUBLICATIONS

First Office Action of the European application No. 19958493.9, issued on Oct. 17, 2024. 8 pages.

* cited by examiner

SAMPLE ANALYZING SYSTEM, METHOD AND CELL IMAGE ANALYZING DEVICE

CROSS-REFERENCE TO RELATED APPLICATIONS

This application is a continuation of International Application No. PCT/CN2019/130608, filed on Dec. 31, 2019, which is incorporated herein by reference in its entirety.

TECHNICAL FIELD

The disclosure relates to medical device technologies and, in particular, to a sample analysis system, a sample analysis method, and a cell image analysis apparatus.

BACKGROUND

At present, a cell image analysis apparatus (such as a slide scanner) can image and analyze a smear of a sample to be analyzed. Before image capturing and analysis for the sample smear, the cell image analysis apparatus displays a mode setting interface in which a user selects a current analysis mode for the cell image analysis apparatus, which images the smear of the sample to be analyzed in this analysis mode using an imaging condition specified by the analysis mode, resulting in low processing efficiency and accuracy of the cell image analysis apparatus.

SUMMARY

Embodiments of the disclosure provide a sample analysis system, a sample analysis method and a cell image analysis apparatus, which are intended to select an imaging condition for a sample to be analyzed based on a blood routine test result of the sample to be analyzed, so as to improve processing efficiency and accuracy.

The technical solutions in the embodiments of the disclosure are implemented as follows.

According to one aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to:

if a value of at least one type of cells in the test result of the sample to be analyzed is less than a preset threshold, control the cell image analysis apparatus to image the smear of the sample to be analyzed under a first imaging condition, so as to obtain images of the at least one type of cells;

if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells;

wherein a number of cell images to be captured by the cell image analysis apparatus under the first imaging condition is greater than that of cell images to be captured under the second imaging condition.

According to another aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to:

if a value of at least one type of cells in the test result of the sample to be analyzed is less than a preset threshold, control the cell image analysis apparatus to image the smear of the sample to be analyzed under a first imaging condition, so as to obtain images of the at least one type of cells;

if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells;

wherein the value of the at least one type of cells includes a value related to a cell volume.

According to still another aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to:

if a value of at least one type of cells in the test result of the sample to be analyzed is less than a preset threshold, control the cell image analysis apparatus to image the smear of the sample to be analyzed under a first imaging condition, so as to obtain images of the at least one type of cells;

if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells, wherein the first imaging condition and the second imaging condition are different from each other in imaging position.

According to still another aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to:

select an analysis mode of the cell image analysis apparatus based on at least one of the test result and sample information of the sample to be analyzed, wherein the analysis mode includes at least one of a white blood cell analysis mode, a red blood cell analysis mode, and a platelet analysis mode, or a combination of at least two of aforesaid modes;

select an imaging condition based on the test result of the sample to be analyzed; and control the cell image analysis apparatus to image the smear of the sample to be analyzed according to the selected imaging condition under the selected analysis mode.

According to still another aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of each sample to be analyzed; and the cell image analysis apparatus configured to image and analyze the smear of the sample to be analyzed, so as to obtain cell images of the sample to be analyzed and an analysis result of the cell images;

wherein the controller is further configured to:

if a value of at least one type of cells in the test result of the sample to be analyzed is less than a preset threshold, control the cell image analysis apparatus image the smear under a first imaging condition, so as to obtain images of the at least one type of cells;

if the value of the at least one type of cells in the test result of the sample to be analyzed is not less than the preset threshold, control the cell image analysis apparatus to image the smear of the sample under a second imaging condition that is different from the first imaging condition, so as to obtain images of the at least one type of cells;

wherein the first imaging condition and the second imaging condition are different from each other in imaging range.

According to still another aspect, an embodiment of the disclosure provides a sample analysis system, including:

a blood cell analyzer configured to test at least one sample to obtain a test result of the at least one sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to: if the test result of the sample to be analyzed indicates presence of abnormal cells, adjust the number of cell images to be captured based on a proportion of the abnormal cells.

According to still another aspect, an embodiment of the disclosure provides a cell image analysis apparatus, including:

an imaging apparatus configured to image a smear of a sample to be analyzed; and a controller configured to obtain a test result of the sample to be analyzed that is obtained by a blood cell analyzer through testing;

wherein the controller is further configured to:

if a value of at least one type of cells in the test result of the sample to be analyzed is less than a preset threshold, control the imaging apparatus to image the smear of the sample to be analyzed under a first imaging condition, so as to obtain images of the at least one type of cells;

if the value of the at least one type of cells in the test result of the sample to be analyzed is not less than the preset threshold, control the imaging apparatus to image the smear of the sample to be analyzed under a second imaging condition that is different from the first imaging condition, so as to obtain images of the at least one type of cells, where the first imaging condition and the second imaging condition are different from each other in at least one of: a number of cell images to be captured, an imaging range size, an imaging position, a power of an objective lens for imaging, and a focus range.

According to still another aspect, an embodiment of the disclosure provides a blood cell analysis method, including:

obtaining a test result of a sample to be analyzed; and if a value of at least one type of cells in the test result of the sample to be analyzed is less than a preset threshold, controlling a cell image analysis apparatus image a smear of the sample to be analyzed under a first imaging condition to, so as to obtain images of the at least one type of cells;

if the value of the at least one type of cells in the test result of the sample to be analyzed is not less than the preset threshold, controlling the cell image analysis apparatus to image the smear of the sample to be analyzed under a second imaging condition that is different from the first imaging condition, so as to obtain images of the at least one type of cells;

wherein a number of cell images to be captured by the cell image analysis apparatus under the first imaging condition is greater than that of cell images to be captured under the second imaging condition.

According to still another aspect, an embodiment of the disclosure provides a blood cell analysis method, including:

obtaining a test result of a sample to be analyzed; and if a volume-related value of at least one type of cells in the test result is less than a preset threshold, controlling a cell image analysis apparatus to image a smear of the sample to be analyzed under a first imaging condition, so as to obtain images of the at least one type of cells;

if the volume-related value of the at least one type of cells in the test result is not less than the preset threshold, controlling the cell image analysis apparatus to image the smear of the sample to be analyzed under a second imaging condition that is different from the first imaging condition, so as to obtain images of the at least one type of cells.

According to still another aspect, an embodiment of the disclosure provides a blood cell analysis method, including:

obtaining a test result of a sample to be analyzed; and if a platelet count in the test result is less than a preset threshold, controlling a cell image analysis apparatus to image a smear of the sample to be analyzed under a first imaging condition, so as to obtain images of the at least one type of cells;

if the platelet count in the test result is not less than the preset threshold, controlling the cell image analysis apparatus to image the smear of the sample to be analyzed under a second imaging condition that is different from the first imaging condition, so as to obtain images of the at least one type of cells;

wherein an imaging position corresponding to the first imaging condition includes a tail portion and/or an edge portion of the smear; and an imaging position corresponding to the second imaging condition includes a body portion of the smear.

According to still another aspect, an embodiment of the disclosure provides a blood cell analysis method, including:

obtaining a test result of a sample to be analyzed and sample information of the sample to be analyzed;

selecting an analysis mode of a cell image analysis apparatus based on at least one of the test result of the sample to be analyzed and the sample information of the sample to be analyzed, wherein the analysis mode includes at least one of a white blood cell analysis mode, a red blood cell analysis mode, and a platelet analysis mode, or a combination of at least two of aforesaid modes;

selecting an imaging condition based on the test result of the sample to be analyzed; and controlling the cell image analysis apparatus to image a smear of the sample to be analyzed according to the selected imaging condition under the selected analysis mode.

According to still another aspect, an embodiment of the disclosure provides a blood cell analysis method, including:

obtaining a test result of a sample to be analyzed; and if a value of at least one type of cells in the test result of the sample to be analyzed is less than a preset threshold, controlling a cell image analysis apparatus to image a smear under a first imaging condition, so as to obtain images of the at least one type of cells;

if the value of the at least one type of cells in the test result of the sample to be analyzed is not less than the preset threshold, controlling the cell image analysis apparatus to image the smear of the sample under a second imaging condition that is different from the first imaging condition, so as to obtain images of the at least one type of cells, where the first imaging condition and the second imaging condition are different from each other in imaging range.

According to still another aspect, an embodiment of the disclosure provides a blood cell analysis method, including:

obtaining a test result of a sample to be analyzed; and if the test result of the sample to be analyzed indicates presence of abnormal cells, adjusting a number of cell images to be captured based on a proportion of the abnormal cells.

According to still another aspect, an embodiment of the disclosure provides a blood cell analysis method, including:

obtaining a test result of a sample analyzed by a blood cell analyzer;

preparing a blood smear of the sample; and if the test result of the sample indicates presence of infected red blood cells, controlling a cell image analysis apparatus to image a region with a relatively thick blood film on the blood smear, so as to detect whether there are malaria parasites, wherein the region with the relatively thick blood film on the blood smear includes a body portion and a tail portion of the blood smear.

According to still another aspect, an embodiment of the disclosure provides a storage medium with executable instructions stored thereon, which is configured to cause a processor to execute the executable instructions to implement at least one of the foregoing blood cell analysis methods.

In the embodiments of the disclosure, the sample analysis system includes a blood cell analyzer, a smear preparation apparatus, a cell image analysis apparatus and a controller. The controller can obtain a test result of at least one sample from the blood cell analyzer, and when a sample of the at least one sample needs to be analyzed by the cell image analysis apparatus, the controller can further control the cell image analysis apparatus based on a value of at least one type of cells in the test result of the sample to be analyzed. One control method is as follows: If the value of the at least one type of cells in the test result of the sample to be analyzed is less than a preset threshold, the cell image analysis apparatus is controlled to image a smear of the sample to be analyzed under a first imaging condition; and if the value of the at least one type of cells in the test result of the sample to be analyzed is not less than the preset threshold, the cell image analysis apparatus is controlled to image the smear of the sample to be analyzed under a second imaging condition that is different from the first imaging condition, wherein a number of cell images to be captured by the cell image analysis apparatus under the first imaging condition is greater than that of cell images to be captured under the second imaging condition, so that the cell image analysis apparatus can automatically select an imaging condition matching a test result for imaging based on different test results of the sample to be analyzed. In this way, the matching imaging condition can be used to specifically capture and analyze cell images of the smear of the sample to be analyzed (for example, specifically image an abnormal part indicated by the test result of the sample to be analyzed), which improves processing efficiency and accuracy of the cell image analysis apparatus and overcomes the current problem of low processing efficiency and accuracy caused by using a same imaging condition for imaging samples to be analyzed.

BRIEF DESCRIPTION OF THE DRAWINGS

In order to more clearly describe the technical solutions in the embodiments of the disclosure or in the prior art, the drawings required for describing the embodiments or the prior art will be briefly described below. Apparently, the drawings in the following description show some of the embodiments of the disclosure, and those of ordinary skill in the art may still derive other drawings from these drawings without involving any inventive effort.

DESCRIPTION OF THE PREFERRED EMBODIMENTS

To make the objectives, technical solutions, and advantages of the disclosure clearer, the disclosure will be described in further detail below with reference to the accompanying drawings. The disclosure shall not be construed as limited to the embodiments provided herein. Instead, the content recorded in the embodiments of the disclosure renders the disclosure comprehensive and complete, and conveys the concept of the embodiments of the disclosure to those skilled in the art. Therefore, all other embodiments derived by those of ordinary skill in the art without involving any inventive effort shall fall within the scope of protection of the disclosure.

It should be noted that, in the embodiments of the disclosure, the terms "comprise", "include", or any other variation thereof are intended to cover a non-exclusive inclusion, such that a method or server including a series of elements includes not only expressly recorded elements, but also other elements not expressly listed, or elements inherent in implementing the method or server. In the absence of more restrictions, an element defined by "including a/an . . . " does not exclude the presence of a further related element in a method or server that includes the element (for example, a step in the method or a unit in the server; the unit, for example, may be a part of a circuit, a part of a processor, a part of a program or software, or the like).

For example, a sample analysis system and apparatus provided in the embodiments of the disclosure include a series of components, but the sample analysis system and apparatus provided in the embodiments of the disclosure are not limited to including the expressly recorded components. Similarly, a blood cell analysis method provided in the embodiments of the disclosure includes a series of steps, but the blood cell analysis method provided in the embodiments of the disclosure is not limited to the recorded steps. It should be noted that "embodiments" involved in the following description describe a subset of all possible embodiments, but it may be understood that the "embodiments" may be the same subset or different subsets of all the possible embodiments, and may be combined with each other without conflict.

Figure 1:
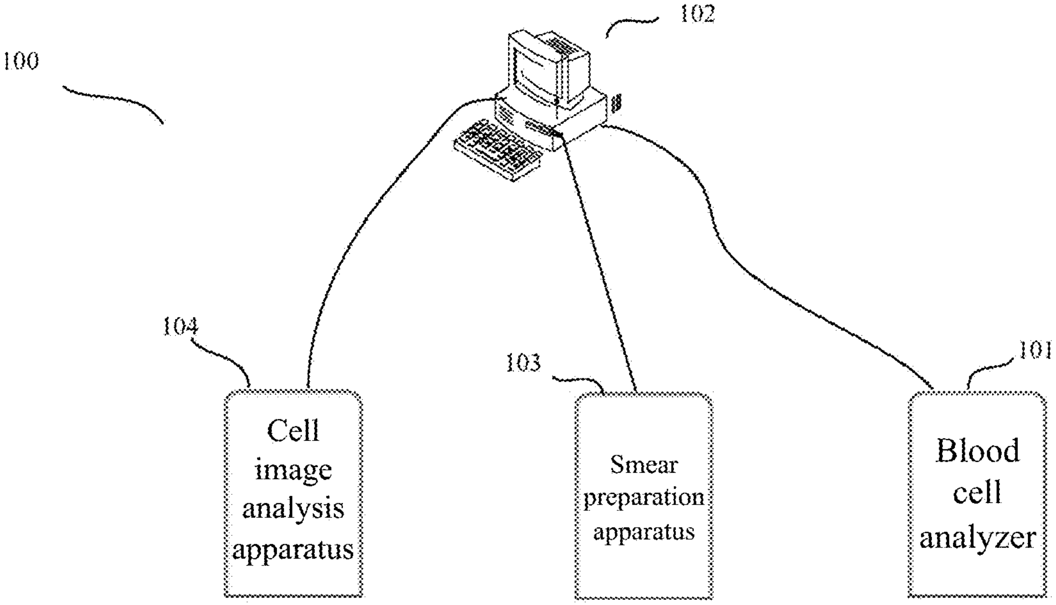
FIG. 1 is an schematic structural diagram of a sample analysis system according to an embodiment of the disclosure.

FIG. 1 shows an optional structure of a sample analysis system according to an embodiment of the disclosure. The sample analysis system 100 shown in FIG. 1 may include a blood cell analyzer 101, a controller 102, a smear preparation apparatus 103 and a cell image analysis apparatus 104.

The blood cell analyzer 101 is configured to test at least one sample to obtain a test result of the at least one sample.

The controller 102 is configured to obtain the test result of the at least one sample. The smear preparation apparatus 103 is configured to prepare a smear for a sample to be analyzed by the cell image analysis apparatus, so as to obtain the smear of the sample to be analyzed. In the embodiments of the disclosure, the sample to be analyzed is a sample that has been tested by the blood cell analyzer and that needs to be further analyzed by the cell image analysis apparatus, and may also be referred to as a sample to be retested. If the test result of a sample tested by the blood cell analyzer triggers a preset microscopic examination rule, the sample will be transported to the smear preparation apparatus 103 for smear preparation, and then be performed with cell image capture and analysis by the cell image analysis apparatus, so that some samples requiring microscopic examination can be retested, which can improve the accuracy of sample test results and reduce sample analysis time. Alternatively, all samples that have been tested by the blood cell analyzer are transported to the smear preparation apparatus 103 for smear preparation, and then are performed with cell image capture and analysis by the cell image analysis apparatus, so that all the samples can be retested, thereby obtaining more accurate and reliable test results.

The cell image analysis apparatus 104 is configured to image and analyze the smear of the sample to be analyzed, so as to obtain cell images of the sample to be analyzed and an analysis result of the cell images.

The controller 102 is further configured to control the cell image analysis apparatus 104 to image the smear of the sample to be analyzed. The control by the controller 102 is implemented in the following manners, but the present disclosure is not limited thereto.

If the test result of the sample to be analyzed indicates presence of primitive/immature cells (blast cells), the number of white blood cell to be imaged is to be increased, for example, the controller 102 instructs the cell image analysis apparatus 104 to increase the imaging region to obtain more white blood cell images. For example, the number of white blood cell to be imaged is 100 in the absence of blast cells, and the number of white blood cell to be imaged is 500 in the presence of blast cells, so as to increase the probability of blast cells being found and improve the sensitivity of testing.

If a platelet count in the test result of the sample to be analyzed is less than a preset threshold, for example, less than $20*10^{\wedge 9}/L$, the controller 102 instructs the cell image analysis apparatus 104 to image a tail portion of the smear, so as to determine whether platelet aggregation has occurred based on cell images of the tail portion, which can help a doctor determine whether the platelet reduction is true or is caused by platelet aggregation, thereby helping the doctor evaluate a patient's bleeding tendency.

If the platelet count is less than the preset threshold, the controller 102 may further instruct the cell image analysis apparatus 104 to image an edge portion of the smear, which may also determine whether platelet aggregation has occurred.

If the test result of the sample to be analyzed indicates presence of fragmented red blood cells, the controller 102 instructs the cell image analysis apparatus 104 to capture cell images in a red blood cell analysis mode. The cell image analysis apparatus 104 may further output the captured cell images (e.g., red blood cell images) and a proportion of fragmented red blood cells, so that a doctor determines whether the presence of fragmented red blood cells is true, confirms the proportion thereof, and issue a report.

If a red blood cell volume in the test result of the sample to be analyzed is less than a preset volume (microcytes are present), e.g., a mean corpuscular volume (MCV) is less than 70 fL, the controller 102 instructs the cell image analysis apparatus 104 to scan red blood cells in a small area on the smear and output the captured cell images, so that a doctor determines whether the presence of microcytes (that is, red blood cells having a volume less than the preset volume) is true based on the cell images, and the cell image analysis apparatus 104 may further output a proportion of microcytes.

If the sample to be analyzed is a sample from a pediatric department and there is no historical medical record, the controller 102 instructs the cell image analysis apparatus 104 to select a combination mode of a white blood cell analysis mode, the red blood cell analysis mode and a platelet analysis mode for imaging, to meet comprehensive retest needs of a first-visit patient at minimum time cost.

If result values of white blood cells, red blood cells, and platelets in the test result of the sample to be analyzed are all lower than respective preset thresholds, for example, a white blood cell (WBC) count is less than $4*10^9$/L, hemoglobin (HGB) is less than 100 g/L, and a platelet count is less than $100*10^9$/L, the controller 102 instructs the cell image analysis apparatus 104 to select a combination mode of the white blood cell analysis mode, the red blood cell analysis mode and the platelet analysis mode for imaging, to meet comprehensive retest needs of the sample to be analyzed at minimum time cost.

If the test result of the sample to be analyzed indicates presence of nucleated red blood cells (NRBC), the controller 102 instructs the cell image analysis apparatus 104 to increase the number of white blood cells to be located and imaged. If the target number of white blood cells to be imaged is set to be 100, according to usual procedures, 1.2 times of the target number of white blood cells are located using a low-power (e.g., 10×) lens, for example, 120 white blood cells are located using the low-power lens, and then a high-power (e.g., 100×) lens is used to image the white blood cells in the located area to obtain the target number of white blood cells. However, for a sample with a high proportion of NRBCs, the number of white blood cells to be imaged may be insufficient. Therefore, the number of white blood cells to be located using the low-power lens may be adjusted based on NRBC result. For example, in the absence of nucleated red blood cells, the number of white blood cell images to be obtained using the low-power objective lens is 120, and 100 white blood cell images can be obtained using the high-power objective lens. In the presence of nucleated red blood cells, especially when there are a large number of nucleated red blood cells (that is, the sample to be analyzed is a sample with a high proportion of nucleated red blood cells), if 120 white blood cell images are still obtained using the low-power objective lens, white blood cell images that can be obtained using the high-power objective lens are less than 100. In this case, it is needed to increase the number of white blood cell images to be obtained using the low-power objective lens, to meet the requirement for the number of white blood cell images to be obtained using the high-power objective lens. If the test result of the sample to be analyzed indicates presence of large platelets, that is, a volume of a platelet is greater than a preset value, the method of increasing the number of white blood cell images to be obtained using the low-power objective lens is also used.

If a red blood cell count in the test result of the sample to be analyzed is less than a preset threshold, the controller 102 instructs or controls the cell image analysis apparatus 104 to expand an imaging range (i.e., increase an imaging area). For example, under normal circumstances, the cell image analysis apparatus 104 can image 1,000 red blood cells in a set fixed region. However, if the red blood cell count is less than the preset threshold, red blood cells that can be imaged in the previous imaging range are less than 1,000. Therefore, the imaging range may be expanded to obtain enough red blood cells.

If the white blood cell count in the test result of the sample to be analyzed is less than the preset threshold, the imaging range is controlled to be expanded. For example, in addition to imaging the body portion of the smear, the cell image analysis apparatus 104 images the edge portion of the smear by extending from the body portion of the smear to the edge portion of the smear, so as to expand the imaging range to obtain the target number of white blood cell images.

If the test result of the sample to be analyzed indicates a classification abnormality, such as a five-classification percentage abnormality, the controller 102 instructs the cell image analysis apparatus 104 to directly use a 40× objective lens, which can improve efficiency. If the test result of the sample to be analyzed indicates presence of abnormal cells, such as blast cells, nucleated red blood cells (NRBC), or abnormal lymphocytes, the 100× lens is still used.

If a volume of a type of cells (such as white blood cells, red blood cells, or platelets) in the test result of the sample to be analyzed is less than a preset threshold, the controller 102 instructs the cell image analysis apparatus 104 to select a small depth of field to capture cell images. If the volume of this type of cells is greater than the preset threshold, a large depth of field may be selected. The test result of the sample tested by the blood cell analyzer includes result values of various test items, histograms, scattergrams, etc. A histogram can reflect a relationship between a cell volume and a cell count or proportion. For example, cell sizes can be discriminated according to forward scatter (FSC) in a histogram of white blood cells, and a larger value of forward scatter intensity indicates a larger cell size. In this embodiment of the disclosure, the cell image analysis apparatus 104 may be controlled to select different depths of field to capture cell images depending on the cell volume. If the cell volume is larger, cell images are captured with a larger depth of field and then fused. For cells having a smaller volume, cell images are captured with a smaller depth of field.

If the test result of the sample to be analyzed indicates presence of platelet aggregation, the controller 102 instructs the cell image analysis apparatus 104 to image the tail portion or edge portion of the smear.

If the platelet (PLT) count in the test result of the sample to be analyzed is high (for example, the PLT count is greater than a set threshold), the controller 102 instructs the cell image analysis apparatus 104 to image a smaller area (that is, reduce the imaging range), and then estimates the PLT count using a graphical method. If the PLT count is less than the set threshold, a larger area may be imaged (that is, the imaging range may be expanded) so that the target number of PLTs can be imaged.

If the test result of the sample to be analyzed indicates presence of red blood cell aggregation, the controller 102 instructs the cell image analysis apparatus to image the tail portion of the smear.

The number of cells to be imaged is selected based on a proportion of abnormal cells in the test result of the sample to be analyzed. The higher the proportion of abnormal cells, the larger the number of cells to be imaged by the cell image analysis apparatus 104. For example, the higher the proportion of nucleated red blood cells (NRBCs), the larger the number of white blood cells that the controller 102 instructs the cell image analysis apparatus 104 to locate and image; and the lower the proportion of NRBCs, the smaller the number of white blood cells to be located and imaged. For example, under normal circumstances, the target number of white blood cells to be imaged is 100. In the absence of abnormal cells, the number of white blood cells to be located and imaged may not be changed. In the presence of abnormal cells, the number of white blood cells to be located is to be adjusted based on the target number of 100 and the proportion of abnormal cells, to correspondingly increase the number of white blood cells to be imaged. For example, if the proportion of NRBCs is 1%, the number of white blood cells to be located is adjusted to 150, and then the located white blood cells are imaged. If the proportion of NRBCs is 2%, the number of white blood cells to be located is adjusted to 200, and then the located white blood cells are imaged. The white blood cells located by the cell image analysis apparatus using the low-power objective lens include white blood cells and suspected white blood cells (such as NRBCs), and if the number of white blood cells located is 100, the higher the proportion of NRBCs, the smaller the number of true white blood cells in the 100 located white blood cells (including suspected white blood cells). Therefore, the higher the proportion of NRBCs, the larger the number of cells that need to be located and imaged.

If the test result of the sample to be analyzed indicates that a proportion of abnormal cells is high, for example, the proportion of abnormal cells is higher than a preset proportion, the controller 102 instructs the cell image analysis apparatus 104 to reduce the number of cells to be imaged, thereby saving time. For example, the test result obtained by the blood cell analyzer shows that neutrophils account for 95%, in this case, the cell image analysis apparatus can find most of the neutrophils by capturing 50 images, with no need to capture more cell images. For the sample analysis system shown in FIG. 1, a detailed description is provided below.

The blood cell analyzer 101 is configured to test at least one sample to obtain a test result of the at least one sample. The at least one sample may be a sample such as a blood sample or a body fluid sample that needs to be tested for the number of cells. For example, the blood cell analyzer 101 can perform a blood routine test on at least one blood sample and/or at least one body fluid sample, so as to test white blood cells (WBCs), red blood cells (RBCs), platelets (PLTs), and other cells in the sample and obtain test results of the WBCs, RBCs, PLTs, and other cells in the sample.

In this embodiment, the blood cell analyzer 101 outputs the test result of the sample after testing the sample. The test result of the sample may be at least one of a cell test parameter of at least one type of cells in the sample and information indicating whether the cell test parameter of the at least one type of cells is abnormal.

The controller 102 is configured to obtain the test result of the at least one sample. The controller 102 may be communicatively connected to the blood cell analyzer 101, and the controller 102 obtains, by means of the communication connection between the two, the test result of the sample that is obtained by the blood cell analyzer. For example, the controller 102 and the blood cell analyzer 101 are connected in a wired or wireless manner, and then the controller 102 obtains, by means of wired or wireless transmission, the test result of the at least one sample that is obtained by the blood cell analyzer.

The controller 102 can obtain respective test results of a plurality of samples, and there may be differences between the test results of the different samples. Therefore, the controller 102 needs to establish a correspondence between the test results of the samples and the samples, so that sample information of the samples is used to identify the test results and to indicate the samples corresponding to the test results. For example, the sample information of a sample includes at least one of a sample number and a subject to which the sample belongs, so that the sample information can uniquely specify the sample.

The smear preparation apparatus 103 is configured to prepare a smear for a sample to be analyzed by the cell image analysis apparatus, so as to obtain the smear of the sample to be analyzed, wherein the smear is a substrate on which a specimen is smeared, for example, a glass slide on which the sample to be analyzed is evenly smeared and cells in the sample are stained.

In this embodiment, the smear preparation apparatus 103 obtains the smear of the sample to be analyzed through operations such as smearing and staining. However, it should be noted that, at present, after a smear of a body fluid sample is prepared, a slide spinning operation needs to be performed to obtain a region having a specific shape such as a circular region in the smear through spinning. In view of this feature of the smear of the body fluid sample, the smear preparation apparatus 103 may include a first preparation apparatus (such as a smearing machine) for preparing a smear of a blood sample and a second preparation apparatus (such as a centrifugal slide spinner) for preparing a smear of a body fluid sample. When the smear preparation apparatus obtains a sample to be analyzed, if the sample to be analyzed is a blood sample, the sample to be analyzed will be transported to the first preparation apparatus (such as the smearing machine); and if the sample to be analyzed is a body fluid sample, the sample to be analyzed will be transported to the second preparation apparatus (such as the centrifugal slide spinner).

For any sample to be analyzed, a correspondence is established between the smear prepared by the smear preparation apparatus 103 and the test result obtained by the blood cell analyzer 101 to indicate that the smear and the test result belong to the same sample to be analyzed. A manner of establishing the correspondence between the two is: corresponding the smear to the test result through the sample information (such as the sample number) of the sample to be analyzed. For example, a label region is provided on the smear and is used to set the sample information. For example, the smear preparation apparatus 103 may obtain the sample information from the blood cell analyzer 101 and provide the sample information in the label region. For example, the smear preparation apparatus 103 has a function of generating a two-dimensional code, displays the sample information in the form of a two-dimensional code, and prints the generated two-dimensional code in the label region.

The sample to be analyzed by the cell image analysis apparatus may be each sample tested by the blood cell analyzer 101. In other words, each sample needs to be analyzed by the cell image analysis apparatus after being tested by the blood cell analyzer 101. Each sample analyzed by the blood cell analyzer 101 is a sample to be analyzed. In this case, a smear of each sample needs to be prepared by the smear preparation apparatus 103. Although this manner consumes a lot of time, sample retests can improve accuracy of test results of samples.

Alternatively, the controller 102 selects a sample that needs to be analyzed by the cell image analysis apparatus based on the test result of the sample, and the sample selected by the controller 102 is the sample to be analyzed. An optional manner of selecting, by the controller 102, a sample to be retested based on the test result of the sample is as follows: the sample to be retested is selected based on the test result of the sample and a preset retest condition, and when the test result of the sample meets the preset retest condition, the controller 102 determines the sample having the test result as the sample to be analyzed, and instructs the smear preparation apparatus 103 to prepare a smear for the sample to be analyzed.

The preset retest condition is used to indicate at least one of: the test result includes an abnormal result indicating that the sample is abnormal, the test result includes a parameter of a specific type of cells, a subject to which the test result belongs is a preset subject of interest, and the sample corresponding to the test result is from a specific department. The parameter of the specific type of cells includes, but is not limited to, a parameter of white blood cells, the preset subject of interest may be, but is not limited to, a patient having a white blood cell disorder, the specific department may be, but is not limited to, a department of reproductive medicine, and so on. The parameter of the specific type of cells, the preset subject of interest, and the specific department may be determined according to medical needs, and are not limited in the embodiments. For example, the preset retest condition includes WBC<2; and if a WBC count in a test result of a sample tested by the blood cell analyzer 101 is 1, and the WBC count is measured in $10^9$/L, the test result of the sample triggers the preset retest condition and is a sample that needs to be retested by the cell image analysis apparatus 104.

The cell image analysis apparatus 104 is configured to image and analyze the smear of the sample to be analyzed, so as to obtain cell images of the sample to be analyzed and an analysis result of the cell images, especially to identify and locate abnormal cells in the smear, and then to image and analyze the abnormal cells that are identified and located.

The cell image analysis apparatus 104 needs to use a specific imaging condition to image the smear of the sample to be analyzed. In this embodiment, the imaging condition is determined by the controller 102, wherein a manner of determining the imaging condition by the controller 102 is: selecting, by the controller 102, the imaging condition based on a relationship between a value of at least one type of cells in the test result and a preset threshold. The selection process is as follows.

If the value of the at least one type of cells in the test result of the sample to be analyzed is less than the preset threshold, the cell image analysis apparatus is controlled to image the smear of the sample to be analyzed under a first imaging condition, so as to obtain images of the at least one type of cells; and if the value of the at least one type of cells in the test result of the sample to be analyzed is not less than the preset threshold, the cell image analysis apparatus is controlled to image the smear of the sample to be analyzed under a second imaging condition that is different from the first imaging condition, so as to obtain images of the at least one type of cells. In this way, the controller 102 selects a matching imaging condition from the first imaging condition and the second imaging condition based on the relationship between the value of the at least one type of cells and the preset threshold.

The value of the at least one type of cells based on which the controller 102 selects the imaging condition may be a value of cells that affects image capturing and analysis by the cell image analysis apparatus. Taking white blood cells as an example, a preset number of white blood cell images need to be captured in the analysis process, and if the captured images are not enough, more images will be captured, otherwise this will affect an analysis result of white blood cells. Therefore, the number of white blood cells in the test result of the sample to be analyzed will affect the image capturing and analysis by the cell image analysis apparatus, and a matching imaging condition needs to be used in this embodiment depending on the number of white blood cells. Based on this, the value of the at least one type of cells includes at least one of a number, a proportion, or a volume of the at least one type of cells.

In an embodiment, a test result of a blood sample tested by the blood cell analyzer 101 usually includes result values of the following test items or test parameters: red blood cell count (RBC), hematocrit (HCT), mean corpuscular volume (MCV), red blood cell distribution width, hemoglobin concentration (HGB), mean corpuscular hemoglobin (MCH), mean corpuscular hemoglobin concentration (MCHC), white blood cell count (WBC), monocyte count (MONO), monocyte ratio (MONO %), neutrophil count (NEUT), neutrophil ratio (NEUT %), lymphocyte count (LY), lymphocyte ratio (LY %), platelet count (PLT), platelet volume distribution width (PDW), mean platelet volume (MPV), platelet-large cell ratio (P-LCR), plateletcrit (PCT), etc. The controller 102 may select an imaging condition based on the result values of these test items or test parameters of the sample to be analyzed, so that the cell image analysis apparatus 104 images cells in the smear of the sample according to the corresponding imaging condition. The test result of the blood sample tested by the blood cell analyzer 101 may further include a histogram, a scattergram, etc., and the cell volume, number, proportion, information about abnormal cells, etc. can also be obtained or identified based on the histogram and the scattergram.

Taking a type of cells as an example, the number of cells of this type represents a count of cells of this type in the test result of the sample to be analyzed, and a count of cells of a certain type of is the number of cells of this type per unit volume. When the sample is tested by the blood cell analyzer, cells that are similar to the cells of this type in morphology may be considered also as cells of this type, and therefore the number of cells of this type represents the total number of cells of this type and suspected cells of this type in the sample to be analyzed.

The proportion of cells of this type represents a ratio of the total number of cells of this type in the sample to be analyzed to the total number of all cells in the sample to be analyzed. If the blood cell analyzer can detect the number of suspected cells of this type in the total number of cells of this type, there are two proportions of this type of cells: One is a ratio of the total number of cells (including suspected ones) of this type to the total number of all the cells in the sample to be analyzed, and the other is a ratio of the number of non-suspected cells of this type in the total number of cells of this type to the total number of cells of this type.

The volume of this type of cells represents a size of this type of cells in the sample to be analyzed. In an actual test process, one sample to be analyzed may include a plurality of cells of this type, and then the volume of this type of cells may be represented by at least one of: a mean volume of this type of cells, a volume range of this type of cells, and a mean volume and a volume range of cells of different levels of this type in the sample to be analyzed, wherein the cell levels may be divided by volume.

The cell number, proportion, and volume are described above by taking one type of cells as an example, but the above description in this embodiment does not limit the scope of protection of the embodiments, and other descriptions of the cell number, proportion, and volume can also be applied to the embodiments.

The value of the at least one type of cells based on which the controller 102 selects the imaging condition may further be a value of a specific type of cells of interest in the analysis process. For example, white blood cells, red blood cells, etc., require attention in the analysis process, and the value of the at least one type of cells includes at least one of a white blood cell count, a red blood cell count and a platelet count, wherein the white blood cells, red blood cells and platelets are specific types of cells.

The corresponding first imaging condition and second imaging condition indicate the manner of capturing the smear of the sample to be analyzed by the cell image analysis apparatus, for example, indicate imaging position (that is, position of the smear to be imaged) and objective lens for imaging (that is, objective lens used for imaging) for the sample to be analyzed. In this embodiment, the first imaging condition and the second imaging condition are different in number of cell images to be captured by the cell image analysis apparatus. For example, the number of cell images to be captured by the cell image analysis apparatus under the first imaging condition is greater than that of cell images to be captured under the second imaging condition.

To be specific, if the value of the at least one type of cells in the test result of the sample to be analyzed is less than the preset threshold, the cell image analysis apparatus is controlled to capture a larger number of cell images; if the value of the at least one type of cells in the test result of the sample to be analyzed is not less than the preset threshold, the cell image analysis apparatus is controlled to capture a smaller number of cell images. How many cell images are to be captured under the first imaging condition and the second imaging condition may depend on retest requirements for this type of cells, which is not limited in the embodiments. For example, when the white blood cell count is lower than the preset threshold, 150 white blood cell images are captured using the first imaging condition; and when the white blood cell count is not lower than the preset threshold, 100 white blood cell images are captured using the second imaging condition.

The number of cell images to be captured under the first imaging condition (a first number for short) and the number of cell images to be captured under the second imaging condition (a second number for short) may be set based on a number of cell images (an initial number for short) set by the cell image analysis apparatus. For example, the first number is obtained by increasing the initial number, that is, the first number is greater than the initial number; and the second number is the same as the initial number or is obtained by decreasing the initial number, that is, the second number is less than the initial number. Alternatively, the first number is the same as the initial number, while the second number is less than the initial number. How much are the increasement and decrement is not limited in the embodiments. The cell image analysis apparatus can image different types of cells, and the initial numbers of the different types of cells are different. Therefore, when the controller 102 controls the cell image analysis apparatus to image, the first number and the second number need to be set with reference to current type of cells to be imaged.

Taking red blood cells (RBC) as an example, a specific number of RBC images, such as 1,000 RBC images, need to be captured during retest, and the cell image analysis apparatus deems that 1,000 RBC images can be obtained using a high-power objective lens after 1.2 times the specific number of images (e.g., 1,200 RBC images) are obtained using a low-power objective lens. However, when the RBC count in the test result is less than the preset threshold, less than 1,000 RBC images can be obtained by capturing 1.2 times the number of images, and then it is considered that cells identified and located are not enough. The application of the controller 102 of this embodiment will increase RBC images to be captured by the cell image analysis apparatus in this case, that is, the cell image analysis apparatus is controlled to capture RBC images of the number of cell images under the first imaging condition, wherein the number of cell images under the first imaging condition is greater than that of cell images set by the cell image analysis apparatus. Similarly, when the RBC count in the test result is not less than the preset threshold, 1,000 RBC images or more can be obtained by capturing 1.2 times the number of images. The application of the controller 102 of this embodiment will maintain or reduce RBC images to be captured by the cell image analysis in this case, that is, the cell image analysis apparatus is controlled to capture RBC images of the number of cell images under the second imaging condition, wherein the number of cell images under the second imaging condition is not greater than that of cell images set by the cell image analysis apparatus, so that the number of cell images to be captured by the cell image analysis apparatus can be controlled based on different test results.

When capturing cell images of the sample to be analyzed, the cell image analysis apparatus will select an imaging range, wherein a size of the imaging range indicates an imaging region of imaging by the cell image analysis apparatus, the imaging region corresponds to a region in the smear, and the region corresponding to the imaging range may be a fixed region or a variable region ("variable" refers to imaging different regions at different times). If the value of the type of cells is less than the preset threshold, cells identified and located may also be not enough when the cell image analysis apparatus performs imaging in the imaging range. In this case, the controller 102 may expand the imaging range (that is, expand the corresponding imaging region) to capture more cell images. Therefore, the controller 102 in this embodiment can adjust the number of cell images to be captured by controlling the size of the imaging range.

In the embodiments of the disclosure, the sample analysis system includes: a blood cell analyzer, a smear preparation apparatus, a cell image analysis apparatus, and a controller. The controller may obtain a test result of at least one sample from the blood cell analyzer, and when a sample of the at least one sample needs to be analyzed by the cell image analysis apparatus, the controller may further control the cell image analysis apparatus based on a value of at least one type of cells in the test result of the sample to be analyzed. One control method is as follows: if the value of the at least one type of cells in the test result of the sample to be analyzed is less than a preset threshold, the cell image analysis apparatus is controlled to image a smear of the sample to be analyzed under a first imaging condition; and if the value of the at least one type of cells in the test result of the sample to be analyzed is not less than the preset threshold, the cell image analysis apparatus is controlled to image the smear of the sample to be analyzed under a second imaging condition that is different from the first imaging condition, wherein the number of cell images to be captured by the cell image analysis apparatus under the first imaging condition is greater than that of cell images to be captured under the second imaging condition, so that the cell image analysis apparatus can automatically select an imaging condition matching a test result for imaging based on different test results of samples to be analyzed. In this way, the matching imaging condition can be used to specifically image and analyze cell images for the smear of the sample to be analyzed (for example, an abnormal part indicated by the test result of the sample to be analyzed is specifically imaged), which improves processing efficiency and accuracy of the cell image analysis apparatus and overcomes the problem of low processing efficiency and accuracy caused by currently using a same imaging condition for imaging samples to be analyzed.

The number of cell images under the first imaging condition used when the value of the at least one type of cells is less than the preset threshold is greater than that of cell images under the second imaging condition. Although this increases imaging time of the cell image analysis apparatus, the cell image analysis apparatus can obtain and analyze more cell images, thereby improving the accuracy of analysis.

For the foregoing sample analysis system shown in FIG. 1, in addition to the number of cell images, the first imaging condition and the second imaging condition are also different from each other in at least one of a size of an imaging range and an imaging position. In other words, the first imaging condition and the second imaging condition are different from each other in at least one of: the number of cell images, the size of the imaging range and the imaging position.

For example, the imaging range for imaging the smear by the cell analysis apparatus under the first imaging condition is larger than that for imaging the smear under the second imaging condition. For example, the imaging range is expanded under the first imaging condition to capture more cell images.

The size of the imaging range under the first imaging condition (a first range for short) and the size of the imaging range under the second imaging condition (a second range for short) may be set based on an imaging range (an initial range for short) set by the cell image analysis apparatus. For example, the first range is obtained by increasing the initial range, that is, the first range is larger than the initial range; and the second range is the same as the initial range or is obtained by decreasing the initial range, that is, the second range is smaller than the initial range. Alternatively, the first range is the same as the initial range, while the second range is smaller than the initial range. The cell image analysis apparatus can image different types of cells, and initial ranges for the different types of cells are different. Therefore, when the controller 102 controls the cell image analysis apparatus to perform imaging, it is required to set the first range and the second range with reference to the current types of cells to be imaged. Alternatively, the controller first sets one of the first range and the second range, and the other is set according to a relationship between the first range and the second range. For example, the second range is first set, and the first range is set by expanding the second range. The specific expansion amount is not limited in the embodiments.

When the cell image analysis apparatus uses the sizes of the imaging ranges under the first imaging condition and the second imaging condition to performing imaging, an imaging position covered by the imaging range under the first imaging condition may be different from that covered by the imaging range under the second imaging condition, so as to obtain cell images at different positions.

Figure 2:
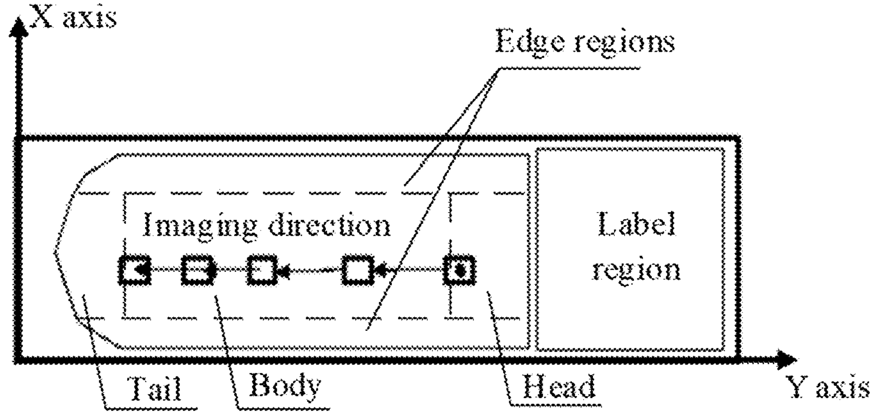
FIG. 2 is a schematic diagram of a smear according to an embodiment of the disclosure.

In addition to the above, the imaging position under the first imaging condition may be different from that under the second imaging condition, wherein the imaging position represents a position at which the cell image analysis apparatus images the smear, and may be any position in the smear. For a smear as shown in FIG. 2, if an imaging direction of the cell image analysis apparatus is from a head portion to a tail portion of the smear, positions in the smear include: head portion, tail portion, body portion, and edge portion, wherein the head portion is at a position in the smear adjacent to a label region, the tail portion is at a position away from the label region, the edge portion includes regions corresponding to the remaining two sides of the smear except the two sides corresponding to the head portion and the tail portion, and the body portion is a region of the smear that lies between the head portion and the tail portion and excludes the edge portion. Alternatively, the head portion and the tail portion may be determined according to the shape of the smear. As shown in FIG. 2, the head portion of the smear is rectangular, and the tail portion of the smear is triangular.

Areas occupied by the head portion, tail portion, and edge portion of the smear in the smear may be determined according to analysis requirements, which is not described in the embodiments. The smear may also be presented in a two-dimensional XY coordinate system, wherein the X direction is a direction of extending from the body portion to the edge portion, and the Y direction is a direction of extending from the body portion to the head portion and the tail portion. FIG. 2 shows a two-dimensional XY coordinate system corresponding to the smear.

The controller 102 selects a matching imaging position based on a relationship between the value of the at least one type of cells in the test result and the preset threshold. In other words, the imaging position of the cell image analysis apparatus for imaging the smear under the first imaging condition is different from that for imaging the smear under the second imaging condition. A difference between the imaging positions may be that the first imaging condition and the second imaging condition are used to image different positions, respectively, for example, the first imaging condition may be used to image the tail portion of the smear, and the second imaging condition may be used to image the body portion of the smear. Alternatively, a difference between the imaging positions may be that the imaging position of one of the first imaging condition and the second imaging condition includes the imaging position of the other imaging condition, for example, the imaging position of the first imaging condition includes the imaging position of the second imaging condition.

Taking white blood cells (WBCs) as an example, the cell image analysis apparatus images the body portion of the smear. If a WBC value (e.g., a count) is less than a preset threshold, cells obtained by imaging the body portion of the smear may be not enough. In this case, the controller 102 instructs or controls the cell image analysis apparatus 104 to adjust the imaging position and extend the imaging position from the body portion to the edge portion, so as to image both the body portion and the edge portion. The expansion of the imaging range is also implemented through extension.

The at least one type of cells referenced by the controller 102 includes platelets (PLTs). The controller 102 may select an imaging condition based on a relationship between a platelet count and a corresponding preset threshold, and the selected imaging condition indicates an imaging position: the controller 102 is configured to, if the platelet count in the test result of the sample to be analyzed is less than the corresponding preset threshold, control the cell image analysis apparatus to use the first imaging condition; or if the platelet count in the test result of the sample to be analyzed is not less than the corresponding preset threshold, control the cell image analysis apparatus to use the second imaging condition.

The imaging position of the cell image analysis apparatus for imaging the smear under the first imaging condition includes the tail portion and/or edge portion of the smear, and the imaging position for imaging the smear under the second imaging condition includes the body portion of the smear.

The preset threshold corresponding to platelets may be determined according to analysis requirements. For example, the preset threshold corresponding to platelets is, but is not limited to, PLT=$20*10^9$/L. If the platelet count is less than the preset threshold, the cell image analysis apparatus needs to image the tail portion and/or the edge portion of the smear. The reason for using such a method is as follows: if the platelet count is less than the preset threshold, platelet aggregation may be present in the sample to be analyzed, therefore, by imaging the tail portion and/or the edge portion to obtain cell images of corresponding regions, and then analyzing the cell images of the tail portion and/or the edge portion, it can be determined whether the decrease in the platelet count (i.e., less than the preset threshold) is caused by platelet aggregation.

By means of the above technical solution, the controller 102 can control the imaging position of the cell image analysis apparatus based on the platelet count, especially can control the cell image analysis apparatus, when the platelet count is less than the corresponding preset threshold, to image at least one of the tail portion and the edge portion, and further determine whether platelet aggregation is present.

Table 1 is taken as an example below to illustrate the sample analysis system shown in FIG. 1. The control of the number of cell images to be captured, the imaging range and the imaging position of the cell image analysis apparatus is described when the value of the at least one type of cells is less than the corresponding preset threshold, wherein "low value" in Table 1 indicates that is the value is less than the preset threshold.

TABLE 1

Imaging conditions for the cell image analysis apparatus

| No. | Value of a type of cells | Imaging condition |
|---|---|---|
| 1 | Low value of RBC | Increase the number of red blood cell images to be captured/the imaging range |
| 2 | Low value of WBC | Increase the number of white blood cell images to be captured/the imaging range/ Extend the imaging position |
| 3 | Low value of PLT | Increase the number of platelet images to be captured/Image the tail portion and/ or the edge portion |

It can be seen from the above Table 1 that, the controller in the sample analysis system can specifically select a matching imaging condition based on a relationship between values of different type of cells and preset thresholds, to control the imaging of the cell image analysis apparatus, so that the cell image analysis apparatus can obtain and analyze cell images matching the test result, which improves processing efficiency and accuracy of the cell image analysis apparatus.

In another embodiment, the sample analysis system as shown in FIG. 1 includes: a blood cell analyzer 101, a controller 102, a smear preparation apparatus 103, and a cell image analysis apparatus 104.

The blood cell analyzer is configured to test at least one sample to obtain a test result of the at least one sample.

The controller is configured to obtain the test result of the at least one sample.

The smear preparation apparatus is configured to prepare a smear for a sample to be analyzed by the cell image analysis apparatus, so as to obtain the smear of the sample to be analyzed.

The cell image analysis apparatus is configured to image and analyze the smear of the sample to be analyzed, so as to obtain cell images of the sample to be analyzed and an analysis result of the cell images.

The controller 102 is further configured to: if a value of at least one type of cells in the test result of the sample to be analyzed is less than a preset threshold, control the cell image analysis apparatus to image the smear of the sample to be analyzed under a first imaging condition, so as to obtain images of the at least one type of cells; if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells, wherein the value of the at least one type of cells includes a value related to cell volume.

In this embodiment, different imaging conditions may be selected based on cell volume. Specifically, if the value related to cell volume is less than the preset threshold, the cell image analysis apparatus is controlled to use the first imaging condition to image the smear of the sample to be analyzed; if the value related to cell volume is not less than the preset threshold, the cell image analysis apparatus is controlled to use the second imaging condition to image the smear of the sample to be analyzed. The value related to cell volume may be, for example, WBC volume, RBC volume, and PLT volume, etc. If the value related to cell volume in the test result of the sample to be analyzed is less than the preset threshold, the cell image analysis apparatus is controlled to use the first imaging condition to perform imaging; and if the value related to cell volume in the test result of the sample to be analyzed is not less than the preset threshold, the cell image analysis apparatus is controlled to use the second imaging condition to perform imaging.

The first imaging condition and the second imaging condition used by the cell image analysis apparatus are different from each other in focus range, wherein the focus range is a longitudinal distance range measured for an object imaged (in this embodiment, the object imaged is the smear of the sample to be analyzed) by the cell image analysis apparatus such that clear cell images can be obtained. A difference between the focus ranges corresponding to the first imaging condition and the second imaging condition may be that the focus range corresponding to the second imaging condition is larger than that corresponding to the first imaging condition. For example, small cells (the value related to cell volume is less than the preset threshold) are imaged using a smaller focus range, and large cells (the value related to cell volume is greater than the preset threshold) are imaged using a larger focus range. Imaging with a larger focus range can ensure clarity of large cells, and imaging small cells with a smaller focus range can not only ensure clarity but also reduce imaging time.

When the cell image analysis apparatus uses the focus range corresponding to the second imaging condition to perform image capturing, the cell image analysis apparatus can capture a plurality of cell images at different depths of field, and then use an image fusion algorithm to fuse all the captured cell images to obtain one cell image.

In this embodiment, the foregoing sample analysis system shown in FIG. 1 can select an imaging condition for the cell image analysis apparatus based on a relationship between the value related to cell volume and the preset threshold, and thereby select a matching imaging condition based on the value related to cell volume in the test result, so that the cell image analysis apparatus can obtain and analyze cell images matching the test result, which improves processing efficiency and accuracy of the cell image analysis apparatus.

In another embodiment, the sample analysis system as shown in FIG. 1 includes: a blood cell analyzer 101, a controller 102, a smear preparation apparatus 103, and a cell image analysis apparatus 104.

The blood cell analyzer is configured to test at least one sample to obtain a test result of the at least one sample.

The controller is configured to obtain the test result of the at least one sample.

The smear preparation apparatus is configured to prepare a smear for a sample to be analyzed by the cell image analysis apparatus, so as to obtain the smear of the sample to be analyzed.

The cell image analysis apparatus is configured to image and analyze the smear of the sample to be analyzed, so as to obtain cell images of the sample to be analyzed and an analysis result of the cell images.

The controller 102 is further configured to: if a value of at least one type of cells in the test result of the sample to be analyzed is less than a preset threshold, control the cell image analysis apparatus image the smear of the sample to be analyzed under a first imaging condition to, so as to obtain images of the at least one type of cells; if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells.

Here, the first imaging condition and the second imaging condition are different from each other in imaging position. The imaging position includes, but is not limited to: the tail portion of the smear, the head portion of the smear, the body portion of the smear, and the edge portion of the smear. For the first imaging condition and the second imaging condition, one of these imaging positions may be selected. Further, these imaging positions may be in one region of the smear. For example, the body portion of the smear is one region, and then different positions in the same region may be selected for the first imaging condition and the second imaging condition.

In this embodiment, for the value of the at least one type of cells, reference may be made to the above related description. If the value of the at least one type of cells includes a platelet count, the process of selecting an imaging condition by the controller 102 is as follows:

If the platelet count is less than the preset threshold, the cell image analysis apparatus is controlled to use the first imaging condition to image the smear of the sample to be analyzed; and if the platelet count is not less than the preset threshold, the cell image analysis apparatus is controlled to use the second imaging condition to image the smear of the sample to be analyzed.

An imaging position corresponding to the first imaging condition includes the tail portion and/or the edge portion of the smear, for example, for the first imaging condition, at least one of the tail portion and the edge portion of the smear is used as the imaging position. An imaging position corresponding to the second imaging condition includes the body portion of the smear. The reason why at least one of the tail portion and the edge portion of the smear is used as the imaging position for the first imaging condition is as follows: if the platelet count is less than the preset threshold, platelet aggregation may be present in the sample to be analyzed, therefore, by imaging the tail portion and/or the edge portion to obtain cell images for the corresponding regions, and then analyzing the cell images of the tail portion and/or the edge portion, it can be determined whether the decrease in the platelet count (i.e., less than the preset threshold) is caused by platelet aggregation. If the platelet count is not less than the preset threshold, it indicates that there may be no platelet aggregation in the sample to be analyzed. In this case, the cell image analysis apparatus may image the body portion of the smear normally. For the description of the tail portion, edge portion and body portion, reference may be made to the above description of FIG. 2.

With the sample analysis system described in this embodiment, the controller can select an imaging position for the cell image analysis apparatus to image the smear based on a relationship between the value of the at least one type of cells in the test result and the preset threshold, so as to select an imaging position matching the value of the at least one type of cells for imaging. In addition, for platelets, a matching imaging position can be selected based on a relationship between the platelet count and the preset threshold, so that when the platelet count decreases, whether platelet aggregation is present in the sample to be analyzed can be determined by capturing the cell images of the tail portion and/or the edge portion.

In another embodiment, the sample analysis system as shown in FIG. 1 includes: a blood cell analyzer 101, a controller 102, a smear preparation apparatus 103, and a cell image analysis apparatus 104.

The blood cell analyzer is configured to test at least one sample to obtain a test result of the at least one sample.

The controller is configured to obtain the test result of the at least one sample.

The smear preparation apparatus 103 is configured to prepare a smear for a sample to be analyzed by the cell image analysis apparatus, so as to obtain the smear of the sample to be analyzed.

The cell image analysis apparatus is configured to image and analyze the smear of the sample to be analyzed, so as to obtain cell images of the sample to be analyzed and an analysis result of the cell images.

The controller 102 is further configured to select an analysis mode of the cell image analysis apparatus based on at least one of the test result and sample information of the sample to be analyzed, wherein the analysis mode includes at least one of: a white blood cell analysis mode, a red blood cell analysis mode, a platelet analysis mode and a combination of at least two of aforesaid modes.

The controller 102 is further configured to select an imaging condition based on the test result of the sample to be analyzed.

The controller 102 is further configured to control the cell image analysis apparatus to image the smear of the sample to be analyzed according to the selected imaging condition in the selected analysis mode.

A difference between the sample analysis system in this embodiment and the foregoing embodiments lies in that: in this embodiment, the controller 102 of the sample analysis system needs to select the analysis mode and the imaging condition for the cell image analysis apparatus, and then control the cell image analysis apparatus based on the selected analysis mode and imaging condition. The controller 102 still selects the imaging condition based on the test result of the sample to be analyzed, but selects the analysis mode based on at least one of the test result and the sample information of the sample to be analyzed, and at least one of the white blood cell analysis mode, the red blood cell analysis mode, the platelet analysis mode and a combination of at least two of aforesaid modes can be selected as the analysis mode of the cell image analysis apparatus, wherein the combination of at least two of aforesaid modes represents at least two modes are selected from the white blood cell analysis mode, the red blood cell analysis mode and the platelet analysis mode as the analysis mode of the cell image analysis apparatus, such that the cell image analysis apparatus can use the selected at least two modes to perform imaging and analysis in the selected at least two modes.

In this embodiment, the blood cell analyzer 101, the smear preparation apparatus 103, and the cell image analysis apparatus 104 can all obtain the sample information of the sample to be analyzed, and the corresponding controller 102 can obtain the sample information of the sample to be analyzed from at least one of the blood cell analyzer 101, the smear preparation apparatus 103 and the cell image analysis apparatus 104. For the description of the sample information of the sample to be analyzed, reference may be made to the foregoing system embodiments, and details are not described again in this embodiment.

In this embodiment, the controller 102 may simultaneously or successively select the analysis mode and the imaging condition for the cell image analysis apparatus. "Successively select" means first selecting one of the analysis mode and the imaging condition, and then selecting the other one. In this way, the controller 102 of the sample analysis system may separately select the analysis mode and the imaging condition for the cell image analysis apparatus, and control the cell image analysis apparatus to image the smear with an imaging condition matching the test result in an analysis mode matching at least one of the test result and the sample information, which achieves automatic selection of the analysis mode and the imaging condition, and improves processing efficiency of the cell image analysis apparatus. In addition, the analysis mode and the imaging condition are selected specifically based on the sample to be analyzed, such that the cell image analysis apparatus works in the matching analysis mode and imaging condition, which improves processing efficiency and accuracy of the cell image analysis apparatus.

The imaging condition selected by the controller 102 is related to at least one of: a number of cell images to be captured (i.e., the above-mentioned number of cell images), a size of an imaging range, an imaging position, a power of an objective lens for imaging, and a focus range, so as to instruct the imaging by the cell image analysis apparatus in these aspects.

The power of the objective lens for imaging indicates an objective lens used by the cell image analysis apparatus when imaging the smear. For example, the power of the objective lens for imaging includes, but is not limited to, at least one of a 10× objective lens, a 40× objective lens, and a 100× objective lens. For the descriptions of the number of cells images to be captured, the imaging range, the imaging position and the focus range, reference may be made to the foregoing system embodiments, and they will also be described in conjunction with the selected analysis mode in this embodiment.

In this embodiment, a manner of selecting the imaging condition by the controller 102 is as follows: the controller selects the imaging condition based on a value of at least one type of cells in the test result of the sample to be analyzed, wherein the value of the at least one type of cells includes at least one of a number, a proportion, and a volume of the type of cells.

For example, the controller selects the imaging condition based on a relationship between the value of the at least one type of cells and a corresponding preset threshold. For example, if the value of the at least one type of cells in the test result of the sample to be analyzed is less than the preset threshold, a first imaging condition is to be selected; if the value of the at least one type of cells in the test result of the sample to be analyzed is not less than the preset threshold, a second imaging condition that is different from the first imaging condition is to be selected.

The number of cell images to be captured corresponding to the first imaging condition is greater than that of cell images to be captured corresponding to the second imaging condition, so that more cell images can be captured when the value (such as a count) of the at least one type of cells decreases. Although such a method increases imaging time of the cell image analysis apparatus, more cell images are obtained, so that more cell images can be analyzed, and the accuracy can be improved. Alternatively, the number of cell images to be captured corresponding to the first imaging condition is less than the number of cell images to be captured corresponding to the second imaging condition, so that the number of cell images to be captured is reduced to reduce imaging time when the value (such as a count) of the at least one type of cells decreases. However, in such a method, cell images obtained by the cell image analysis apparatus is also reduced, and fewer cell images can be analyzed by the cell image analysis apparatus, which reduces accuracy.

In addition to the number of cell images to be captured, the first imaging condition and the second imaging condition may be different from each other in other aspects. For example, the imaging range of the cell image analysis apparatus for imaging the smear under the first imaging condition is larger than that for imaging the smear under the second imaging condition; or the imaging position of the cell image analysis apparatus for imaging the smear under the first imaging condition is different from that for imaging the smear under the second imaging condition. For details, reference may be made to the description in the foregoing system embodiments.

Analysis modes and related imaging conditions that match three types of cells, namely white blood cells, red blood cells and platelets, are separately described below.

White Blood Cells

If the test result of the sample to be analyzed includes abnormality information related to white blood cells, the controller 102 selects the white blood cell analysis mode or a combination mode including the white blood cell analysis mode. In other words, the controller may select only the white blood cell analysis mode as the analysis mode of the cell image analysis apparatus, or select at least one of the red blood cell analysis mode and the platelet analysis mode in addition to selecting the white blood cell analysis mode. Although the method of selecting at least two modes increases a processing time of the cell image analysis apparatus, more types of cells are analyzed by the cell image analysis apparatus, which enriches the analysis result.

In this embodiment, the abnormality information related to white blood cells may include, but is not limited to: abnormality information indicating that a white blood cell count deviates from a normal range, or indicating presence of abnormal cells related to white blood cells, wherein the white blood cell count being lower than the normal range indicates a decrease in the number of white blood cells in the sample to be analyzed, and the white blood cell count being higher than the normal range indicates an increase in the number of white blood cells in the sample to be analyzed; and the abnormal cells related to white blood cells include, but are not limited to, primitive/immature cells (blast cells), immature granulocytes, abnormal lymphocytes, nucleated red blood cells, etc.

In this embodiment of the disclosure, if the test result of the sample includes abnormality information related to white blood cells, the white blood cell analysis mode or a combination mode including the white blood cell analysis mode is to be selected. In the white blood cell analysis mode, the cell image analysis apparatus can image a target number of white blood cells, so as to further analyze information related white blood cells of the sample.

In addition to selecting the analysis mode based on the abnormality information, since the abnormality information related to white blood cells affects a white blood cell imaging and analysis result of the cell image analysis apparatus, a more specific imaging condition may be further selected based on the abnormality information. For example, after the white blood cell analysis mode is selected, a first imaging condition is to be selected if the abnormality information related to white blood cells indicates that the white blood cell count is lower than a first preset threshold or indicates presence of abnormal cells related to white blood cells; a second imaging condition is to be selected if the abnormality information related to white blood cells indicates that the white blood cell count is not lower than (i.e., not less than) the first preset threshold or indicates that there are no abnormal cells related to white blood cells.

The number of white blood cell images to be captured corresponding to the first imaging condition is greater than the number of white blood cell images to be captured corresponding to the second imaging condition. Therefore, when the white blood cell count decreases or abnormal cells related to white blood cells are present, the number of white blood cell images to be captured is to be increased. The number of white blood cell images to be captured represents the cell image number of white blood cells captured by the cell image analysis apparatus, and for the description thereof, reference may be made to the related description in the foregoing system embodiments. The imaging condition for the abnormality information related to white blood cells is described below in different examples.

When the test result of the sample to be analyzed indicates presence of immature cells, if the cell image analysis apparatus continues to capture the number of white blood cell images in the absence of immature cells, the number of white blood cells will be not enough, and immature cells are not easily found. In this case, the controller 102 controls the cell image analysis apparatus to continue to capture the number of white blood cell images to be captured under the first imaging condition, so as to increase the number of white blood cell images captured in the absence of immature cells. For example, the number of white blood cell images to be captured in the absence of immature cells is 100, and then the number of white blood cell images to be captured in the presence of immature cells is 200. By increasing the number of white blood cell images to be captured, a probability of finding immature cells is increased, and analysis sensitivity is improved.

No nucleated red blood cells are present in a normal sample, or a proportion of nucleated red blood cells (also referred to as a cell ratio) is a preset proportion (such as 0). For the normal sample, the cell image analysis apparatus sets a target number, wherein the target number is the number of white blood cells that need to be imaged with a high-power objective lens (such as a 100× objective lens). Therefore, for the normal sample, if the target number of white blood cells are identified and located with a low-power objective lens, the target number of white blood cells can also be imaged with the high-power objective lens. However, if nucleated red blood cells are present in a sample, or a proportion of nucleated red blood cells is greater than the preset proportion, when the target number of white blood cells are identified and located with the low-power objective lens, less than the target number of white blood cell images may be imaged with the high-power objective lens. In this case, the controller increases the number of white blood cells to be identified and located with the low-power objective lens. That is, in this case, the controller controls the cell image analysis apparatus to perform imaging under the first imaging condition, increasing the number of white blood cell images to be captured with the low-power objective lens, and thereby meeting requirements on the target number using the high-power objective lens.

Taking white blood cells (WBCs) as an example, the cell image analysis apparatus images the body portion of the smear. If the WBC count is less than the first preset threshold, the controller also needs to increase the number of white blood cell images to be captured. Generally, the cell image analysis apparatus may image the body portion of the smear to obtain WBCs. If the WBC count is less than the first preset threshold, cells obtained may be not enough. In this case, the controller 102 adjusts the imaging position and extends the imaging position from the body portion to the edge portion, so as to image both the body portion and the edge portion, thereby expanding the imaging range by the extending, and the expansion of the imaging range may increase the number of images captured. Therefore, a method of increasing the number of images to be captured in this embodiment may be expanding the imaging range, which is not described one by one in this embodiment.

Form the above description of white blood cells, the controller can select a matching analysis mode and imaging condition based on the abnormality information related to white blood cells, so as to adapt to the analysis of white blood cells.

Red Blood Cells

If the test result of the sample to be analyzed includes abnormality information related to red blood cells, the controller 102 selects the red blood cell analysis mode or a combination mode including the red blood cell analysis mode.

In this embodiment, the abnormality information related to red blood cells is used to indicate the presence of abnormal red blood cells in the sample to be analyzed. For example, the abnormality information related to red blood cells includes, but is not limited to, at least one of: a red blood cell count deviating from the normal range, red blood cell aggregation, fragmented red blood cells and a red blood cell volume being less than a preset volume. The red blood cell aggregation indicates that some red blood cells in the sample to be analyzed are aggregated in one region. The presence of fragmented red blood cells indicates that morphologically incomplete red blood cells are present in the sample to be analyzed. The red blood cell volume being less than the preset volume indicates that microcytes are present in the sample to be analyzed. For example, the preset volume may be, but is not limited to, 70 fL (femtoliters). If the red blood cell volume MCV is less than 70 fL, it indicates that microcytes are present in the sample to be analyzed. When the test result includes theses abnormality information, the controller selects the red blood cell analysis mode or a combination mode including the red blood cell analysis mode as the analysis mode of the cell image analysis apparatus, and control the cell image analysis apparatus to scan the smear in the selected mode to obtain image cells.

For the two abnormalities, namely the fragmented red blood cells and the red blood cell volume being less than the preset volume, the cell image analysis mode may further output at least one of a proportion of fragmented red blood cells and a proportion of microcytes, so that whether fragmented red blood cells are present in the sample to be analyzed is determined based on the proportion of the fragmented red blood cells, and whether microcytes are present in the sample to be analyzed is determined based on the proportion of microcytes.

A method of determining whether fragmented red blood cells are present in the sample to be analyzed is as follows: a criterion for determining whether fragmented red blood cells are present is set in the cell image analysis apparatus, and whether fragmented red blood cells are present is determined based on the proportion of fragmented red blood cells in the sample to be analyzed and the determination criterion. For example, the determination criterion is a preset proportion indicating the absence of fragmented red blood cells. If the proportion of fragmented red blood cells in the current sample to be analyzed is greater than the preset proportion, it indicates that fragmented red blood cells are present, and if the proportion of fragmented red blood cells in the current sample to be analyzed is not greater than the preset proportion, it indicates that no fragmented red blood cells are present. A method of determining whether microcytes are present in the sample to be analyzed is similar to the method of determining whether fragmented red blood cells are present in the sample to be analyzed, and details are described in this embodiment.

For the above abnormality information related to red blood cells, the controller may further select different imaging conditions. If the abnormality information related to red blood cells includes red blood cell aggregation, the controller controls the cell image analysis apparatus to image the tail portion of the smear to obtain cell images of the tail portion of the smear, so that the distribution of cells in the tail portion is identified based on the cell images of the tail portion, to determine whether red blood cell aggregation is present in the sample to be analyzed.

If the red blood cell volume is less than the preset volume, the controller controls the cell image analysis apparatus to scan red blood cells in a small area on the smear. In other words, if the red blood cell volume is less than the preset volume, the controller needs to control the imaging range of the cell image analysis apparatus to control the cell image analysis apparatus to scan red blood cells within a small imaging range. The smaller the imaging range, the shorter imaging time of the cell image analysis apparatus. Therefore, such control can save working time of the cell image analysis apparatus.

From the above description of red blood cells, the controller can select a matching analysis mode and imaging condition based on the abnormality information related to red blood cells, and the cell image analysis apparatus uses the matching analysis mode and imaging condition to analyze the red blood cells in the sample to be analyzed.

Platelets

If the test result of the sample to be analyzed includes abnormality information related to platelets, the controller selects the platelet analysis mode or a combination mode including the platelet analysis mode, so as to use the platelet analysis mode, or use the platelet analysis mode and one of other analysis modes as the analysis mode of the cell image analysis apparatus.

The abnormality information related to platelets is used to indicate the presence of abnormal platelets in the sample to be analyzed. The abnormality information related to platelets includes, but is not limited to, at least one of platelet aggregation and a platelet count being lower than (less than) a second preset threshold. Based on the abnormality information, the cell image analysis apparatus at least uses the platelet analysis mode to perform imaging and analyzing.

For the above abnormality information related to platelets, the imaging condition that can be used by the controller may be the following condition.

The controller selects the first imaging condition if the platelet count is less than the second preset threshold; and the controller selects the second imaging condition if the platelet count is not lower than (i.e., not less than) the second preset threshold, wherein an imaging position or imaging range corresponding to the first imaging condition is different from that corresponding to the second imaging condition. In other words, the controller controls one of the imaging position and imaging range of the smear based on a relationship between the platelet count and the second preset threshold.

If the imaging range is controlled, the imaging range under the first imaging condition is larger than the imaging range under the second imaging condition. The reason is as follows: if the platelet count is less than the second preset threshold, it indicates that the platelet count in the sample to be analyzed may decrease and that platelets in the sample to be analyzed may decrease, and then a larger region needs to be imaged to increase a probability of imaging enough platelets; if the platelet count is not less than the second preset threshold, it indicates that the platelet count in the sample to be analyzed may increase and that platelets in the sample to be analyzed may increase, and then enough platelets may be imaged by imaging a smaller region. Therefore, the imaging range under the first imaging condition is larger than the imaging range under the second imaging condition.

If the imaging position is controlled, the imaging position corresponding to the first imaging condition includes the tail portion and/or the edge portion of the smear, so as to obtain cell images of the tail portion and/or the edge portion, and determine whether platelet aggregation is present in the sample to be analyzed and whether the decrease in the platelet count is caused by platelet aggregation, based on the obtained cell images. The imaging position corresponding to the second imaging condition includes the body portion of the smear. Since the platelet count under the second imaging condition does not decrease, the body portion of the smear may be imaged normally.

The selection of the analysis mode and the imaging condition by the controller is described above from the perspective of the abnormality information related to white blood cells, the abnormality information related to red blood cells, and the abnormality information related to platelets. In addition to the above selection methods, the controller may further select the analysis mode or the imaging condition with reference to other aspects.

One method of selecting the analysis mode: the controller selects the analysis mode based on results corresponding to white blood cells, red blood cells and platelets in the test result. For example, if the white blood cell count, the red blood cell count and the platelet count in the test result of the sample to be analyzed are all less than respective preset thresholds, the controller selects the white blood cell analysis mode, the red blood cell analysis mode and the platelet analysis mode, so that the cell image analysis apparatus can successively use the white blood cell analysis mode, the red blood cell analysis mode and the platelet analysis mode. The using sequence of these three cell analysis modes is not limited in this embodiment.

It should be noted here that, when the controller selects the analysis mode based on the white blood cell count, the red blood cell count and the platelet count, the preset thresholds referenced correspond to respective types of cells. For example, respective test values related to white blood cells, red blood cells and platelets in the sample to be analyzed are respectively: WBC=$3.0*10^9$/L, HGB=$80*10^9$/L, and PLT=$95*10^9$/L; if the controller determines that the respective counts of the three types of cells are all less than the respective preset thresholds: WBC<$4*10^9$/L, HGB<100 g/L, and PLT<$100*10^9$/L, the controller selects a combination mode of the white blood cell analysis mode, the red blood cell analysis mode and the platelet analysis mode, so that the cell image analysis apparatus comprehensively analyzes the sample to be analyzed at the minimum time cost.

Another method of selecting the analysis mode: the controller is configured to select the analysis mode based on the sample information. A method of selecting the analysis mode based on the sample information is as follows: a combination mode of the white blood cell analysis mode, the red blood cell analysis mode and the platelet analysis mode is selected if the sample information includes information indicating that the sample to be analyzed is from a pediatric department and there is no historical medical record. In this way, for a sample of a first-visit patient from a pediatric department, the cell image analysis apparatus can analyze the sample in the three analysis modes: the white blood cell analysis mode, the red blood cell analysis mode and the platelet analysis mode, so that the cell image analysis apparatus comprehensively analyzes the sample to be analyzed at the minimum time cost. If a sample of a first-visit patient from another department also needs to be fully analyzed, the controller of this embodiment may also select the white blood cell analysis mode, the red blood cell analysis mode and the platelet analysis mode for the sample of the first-visit patient from the another department.

One method of selecting the imaging condition: the controller presets at least two types of abnormality information and an imaging condition corresponding to each type of the abnormality information based on test results of historical samples. In this way, after obtaining a test result of any sample to be analyzed, the controller determines whether the preset abnormality information is present based on the test result of the sample to be analyzed. If a first type of abnormality information is present, the first imaging condition is to be selected; and if a second type of abnormality information is present, the second imaging condition that is different from the first imaging condition is to be selected. In this way, the selection of the imaging condition by the controller is controlled based on the preset abnormality information and imaging condition for the sample to be analyzed, wherein the abnormality information and imaging condition preset by the controller may be realized through human-machine interaction. For example, the abnormality information and imaging condition is set by a user in a display interface corresponding to the controller, to allow user intervention, thereby improving flexibility and convenience.

The first type of abnormality information is different from the second type of abnormality information in degree of abnormality. The higher the degree of abnormality, the higher the requirements for the cell image analysis apparatus and the higher the processing priority; the lower the degree of abnormality, the lower the requirements for the cell image analysis apparatus and the processing can be delayed. Several types of abnormality information are taken as examples for description below.

One example: the first type of abnormality information includes an abnormal cell prompt or alarm, and the abnormal cell prompt or alarm includes, but is not limited to, a blast cell alarm, a nucleated red blood cell alarm, etc. In the case of the first type of abnormality information, the first imaging condition includes selecting a first objective lens to image the smear of the sample to be analyzed. The second type of abnormality information includes information about a cell classification proportion abnormality, such as a white blood cell classification abnormality. In this case, the second imaging condition includes selecting a second objective lens to image the smear of the sample to be analyzed, wherein a power of the first objective lens is higher than that of the second objective lens. Therefore, for the first type of abnormality information, the cell image analysis apparatus is controlled to use a higher-power objective lens to magnify cells corresponding to the first type of abnormality information by a larger magnification power, so as to facilitate the observation of the cells. For the second type of abnormality information, a lower-power objective lens may be used. Because the degree of abnormality of the second type of abnormality information is lower than that of the first type of abnormality information, the second type of abnormality information can be rechecked without a larger magnification power.

In this embodiment, the power of the first objective lens may be, but is not limited to, 100×, and the power of the second objective lens may be, but is not limited to, 40×. In an actual analysis process, the power of the first objective lens and the power of the second objective lens may be determined according to analysis requirements, but a relationship between the powers of the first objective lens and the second objective lens satisfies that the power of the first objective lens is higher than (i.e., greater than) the power of the second objective lens.

Another example: the first type of abnormality information includes a proportion of abnormal cells related to white blood cells being less than a preset proportion, the second type of abnormality information includes a proportion of abnormal cells related to white blood cells being not less than a preset proportion, and the number of white blood cell images to be captured corresponding to the first imaging condition is less than that of white blood cell images to be captured corresponding to the second imaging condition.

The abnormal cells related to white blood cells will affect the number of white blood cells obtained in the analysis process. For example, a proportion of nucleated red blood cells related to white blood cells in a normal sample is 0. In this case, the cell image analysis apparatus obtains a (preset) target number of white blood cell images to be captured in the analysis process. However, if the proportion of nucleated red blood cells is greater than 0, a nucleated red blood cell image may be considered as a white blood cell image during imaging. Therefore, if the target number of white blood cell images to be captured are still obtained, there are less than the target number of true white blood cell images in these images. In this case, a number of white blood cell images greater than the target number needs to be captured. Therefore, in this embodiment, the corresponding number of white blood cell images to be captured when the proportion of abnormal cells related to white blood cells is less than the preset proportion is less than the corresponding number of white blood cell images to be captured when the proportion of abnormal cells related to white blood cells is not less than the preset proportion, so as to meet requirements of the cell image analysis apparatus for white blood cell images during analysis.

Still another example: if a proportion of abnormal cells is high, the number of cells to be imaged is reduced to reduce imaging time.

For example, if a proportion of neutrophils is 95%, the cell image analysis apparatus captures a small number of cell images. For example, most of neutrophils can be imaged by capturing 50 cell images, thereby reducing imaging time of the cell image analysis apparatus while imaging neutrophils.

Another method of selecting the imaging condition: if the selected analysis mode is the white blood cell analysis mode or a combination mode including the white blood cell analysis mode, the controller determines whether the number of red blood cells is less than a preset threshold based on the test result. If the number of red blood cells is less than the preset threshold, the first imaging condition is selected to capture white blood cell images; and if the number of red blood cells is not less than the preset threshold, the second imaging condition is selected to capture white blood cell images. An imaging position of the first imaging condition is different from that of the second imaging condition, thereby determining capturing of white blood cell images by determining the number of red blood cells.

For example, when the number of red blood cells is less than the preset threshold, the imaging position corresponding to the first imaging condition includes a junction of the body portion and the tail portion of the smear (a body-tail junction for short); and when the number of red blood cells is not less than the preset threshold, the imaging position corresponding to the second imaging condition includes the body portion of the smear.

The selection of the analysis mode by the controller based on at least one of the test result and the sample information and the selection of the imaging condition based on the test result are described above. For a better understanding, the foregoing selections of the analysis mode and the imaging condition are listed one by one in the form of a table. In some examples, no imaging condition or analysis mode is described, and it is considered that the cell image analysis apparatus makes no modification to the situations of these examples. However, the table is only an enumeration of some examples, and shall not be construed as limiting the scope of protection of the embodiments.

TABLE 2

Selection table for analysis modes and imaging conditions

| No. | Test result and/or sample information | Analysis mode | Imaging condition |
|---|---|---|---|
| 1 | Low platelet count (less than the second preset threshold) | Platelet analysis mode or a combination mode including the platelet analysis mode | Increase the imaging range |
| 2 | Low platelet count (less than the second preset threshold) | Platelet analysis mode or a combination mode including the platelet analysis mode | The imaging position includes the tail portion and/or the edge portion |
| 3 | Red blood cell aggregation | Red blood cell analysis mode or a combination mode including the red blood cell analysis mode | The imaging position includes the tail portion |
| 4 | Fragmented red blood cells | Red blood cell analysis mode or a combination mode including the red blood cell analysis mode | |
| 5 | The red blood cell volume is less than the preset volume | Red blood cell analysis mode or a combination mode including the red blood cell analysis mode | Reduce the imaging range |

TABLE 2-continued

Selection table for analysis modes and imaging conditions

| No. | Test result and/or sample information | Analysis mode | Imaging condition |
|---|---|---|---|
| 6 | Low white blood cell value or the presence of abnormal cells related to white blood cells | White blood cell analysis mode or a combination mode including the white blood cell analysis mode | Increase the number of white blood cell images to be captured/Increase the imaging range |
| 7 | Values of white blood cells, red blood cells, and platelets are all low | A combination mode of the white blood cell analysis mode, the red blood cell analysis mode and the platelet analysis mode | |
| 8 | Sample of a first-visit patient from a pediatric department | A combination mode of the white blood cell analysis mode, the red blood cell analysis mode and the platelet analysis mode | |
| 9 | Abnormality information prompt or alarm | | Image with the first objective lens |
| 10 | Cell classification proportion abnormality | | Image with the second objective lens, wherein the power of the first objective lens is higher than that of the second objective lens |
| 11 | High proportion of abnormal cells (NRBC) related to white blood cells | | Increase the number of white blood cell images to be captured |
| 12 | High abnormality alarm level or high proportion of abnormal cells | | Reduce the number of cell images to be captured |
| 13 | Low red blood cell value | White blood cell analysis mode or a combination mode including the white blood cell analysis mode | Image white blood cells, and image the junction of the body portion and the tail portion of the smear |

In another embodiment, the sample analysis system as shown in FIG. 1 includes: a blood cell analyzer 101, a controller 102, a smear preparation apparatus 103, and a cell image analysis apparatus 104.

The blood cell analyzer is configured to test at least one sample to obtain a test result of the at least one sample.

The controller is configured to obtain the test result of the at least one sample.

The smear preparation apparatus is configured to prepare a smear for a sample to be analyzed by the cell image analysis apparatus, so as to obtain the smear of each sample to be analyzed.

The cell image analysis apparatus is configured to image and analyze the smear of the sample to be analyzed, so as to obtain cell images of the sample to be analyzed and an analysis result of the cell images.

The controller 102 is further configured to: if a value of at least one type of cells in the test result of the sample to be analyzed is less than a preset threshold, control the cell image analysis apparatus to image the smear under a first imaging condition, so as to obtain images of the at least one type of cells; if the value of the at least one type of cells in the test result of the sample to be analyzed is not less than the preset threshold, control the cell image analysis apparatus to image the smear of the sample under a second imaging condition that is different from the first imaging condition, so as to obtain images of the at least one type of cells.

An imaging range corresponding to the first imaging condition is different from that corresponding to the second imaging condition.

A difference between the sample analysis system and the sample analysis system described above lies in that: in this embodiment, the controller of the sample analysis system controls the imaging range of the cell image analysis apparatus based on a relationship between the value of the at least one type of cells in the test result and the preset threshold, such that the imaging range is different in different situations. For example, the imaging range corresponding to the first imaging condition is larger than that corresponding to the second imaging condition. The value of the at least one type of cells includes, but is not limited to, the number of white blood cells, the number of red blood cells, or the number of platelets. For example, if the white blood cell value of the sample to be analyzed is low, that is, the white blood cell count is less than the preset threshold, the imaging range for imaging the smear of the sample is expanded to obtain a target number (e.g., 100) of white blood cells in a larger imaging range.

In the foregoing sample analysis system shown in FIG. 1, the differences between the imaging ranges corresponding to the first imaging condition and the second imaging condition are described. In this embodiment, reference may be made to the above description, and details are not described again in this embodiment.

Another implementation corresponding to the sample analysis system shown in FIG. 1 is as follows:

The blood cell analyzer 101 is configured to test at least one sample to obtain a test result of the at least one sample.

The controller 102 is configured to obtain the test result of the at least one sample.

The smear preparation apparatus 103 is configured to prepare a smear for a sample to be analyzed by the cell image analysis apparatus, so as to obtain the smear of the sample to be analyzed.

The cell image analysis apparatus 104 is configured to image and analyze the smear of the sample to be analyzed, so as to obtain cell images of the sample to be analyzed and an analysis result of the cell images.

The controller 102 is further configured to:

if the test result of the sample to be analyzed indicates presence of abnormal cells, adjust the number of cell images to be captured based on a proportion of abnormal cells or abnormality alarm information. The abnormality alarm information includes information representing the proportion of abnormal cells, and the abnormal cells include NRBCs or blast cells, wherein the proportion of abnormal cells is positively or negatively correlated with the number of cell images to be captured. If the abnormal cells include nucleated red blood cells, adjusting the number of cells to be located and imaged based on a proportion of abnormal cells includes adjusting the number of white blood cells to be located and imaged based on a proportion of nucleated red blood cells, wherein the higher the proportion of nucleated red blood cells, the larger the number of white blood cells to be located. In other words, if the test result of the sample to be analyzed indicates presence of NRBCs, the higher the proportion of NRBCs, the larger the number of cells (e.g., white blood cells) to be located and imaged by the cell image analysis apparatus 104. For example, if the proportion of NRBCs is 1%, the cell image analysis apparatus 104 locates 150 white blood cells (including suspected white blood cells) and images the located cells; and if the proportion of NRBCs is 2%, the cell image analysis apparatus 104 locates 200 white blood cells (including suspected white blood cells) and images the located cells. If the abnormal cells are blast cells, and a proportion of blast cells is high, it may not be necessary to image a lot of cells to identify the blast cells; and if the proportion of blast cells is very low, it may be necessary to image more cells to avoid missed detection due to the low proportion of cells.

The abnormal cells include blast cells; and adjusting the number of cells to be located and imaged based on a proportion of abnormal cells includes adjusting the number of cells to be located and imaged based on a proportion of blast cells, wherein the higher the proportion of blast cells, the smaller the number of cells to be located and imaged; and the lower the proportion of blast cells, the larger the number of cells to be located and imaged.

For detailed description, refer to the related descriptions in the foregoing embodiments, and details are not described again in this embodiment.

Figure 3:
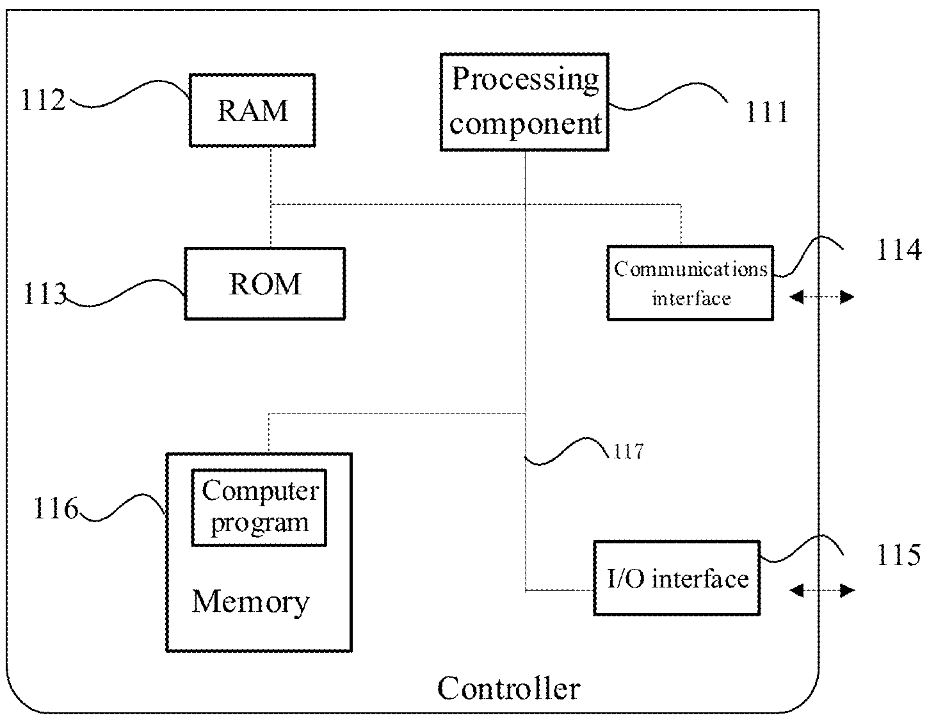
FIG. 3 is an schematic structural diagram of a controller in a sample analysis system according to an embodiment of the disclosure.

For the foregoing sample analysis system shown in FIG. 1, an optional structure of the controller in each sample analysis system is shown in FIG. 3, at least including: a processing component 111, a RAM 112, a ROM 113, a communication interface 114, a memory 116, and an I/O interface 115, wherein the processing component 111, the RAM 112, the ROM 113, the communication interface 114, the memory 116, and the I/O interface 115 communicate via a bus 117.

The processing component may be a CPU, a GPU, or another chip having a computing capability.

The memory 116 contains an operating system, and various computer programs such as an application program executable by the processor component 111, and data required for execution of the computer programs. In addition, in the process of sample analysis, any information that needs to be stored locally may be stored in the memory 116.

The I/O interface 115 is composed of a serial interface such as USB, IEEE 1394, or RS-232C, a parallel interface such as SCSI, IDE, or IEEE 1284, and an analog signal interface composed of a D/A converter, an A/D converter, etc. An input device composed of a keyboard, a mouse, a touchscreen, or another control button is connected to the I/O interface 115, and a user may directly input data to the controller 110 by using the input device. In addition, the I/O interface 115 may be further connected to a display having a display function, such as: a liquid crystal display, a touchscreen, an LED display, etc., and the controller may output information to the display for displaying in the form of image, for example: an analysis mode and a test result.

The communication interface 114 may be an interface of any communication protocol currently known. The communication interface 114 communicates with outside over a network. The controller may communicate, through the communication interface 114 and based on a communication protocol, data with any apparatus connected over the network.

Figure 4:
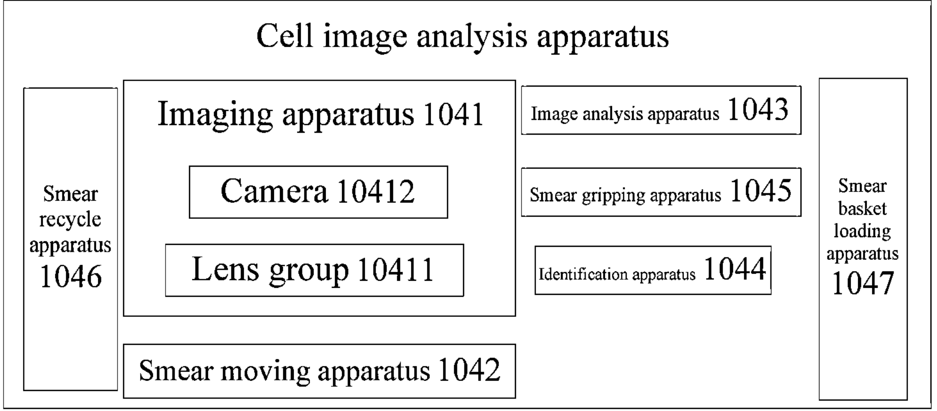
FIGS. 4 and 5 are schematic structural diagrams of a cell image analysis apparatus in a sample analysis system according to an embodiment of the disclosure.
Figure 5:
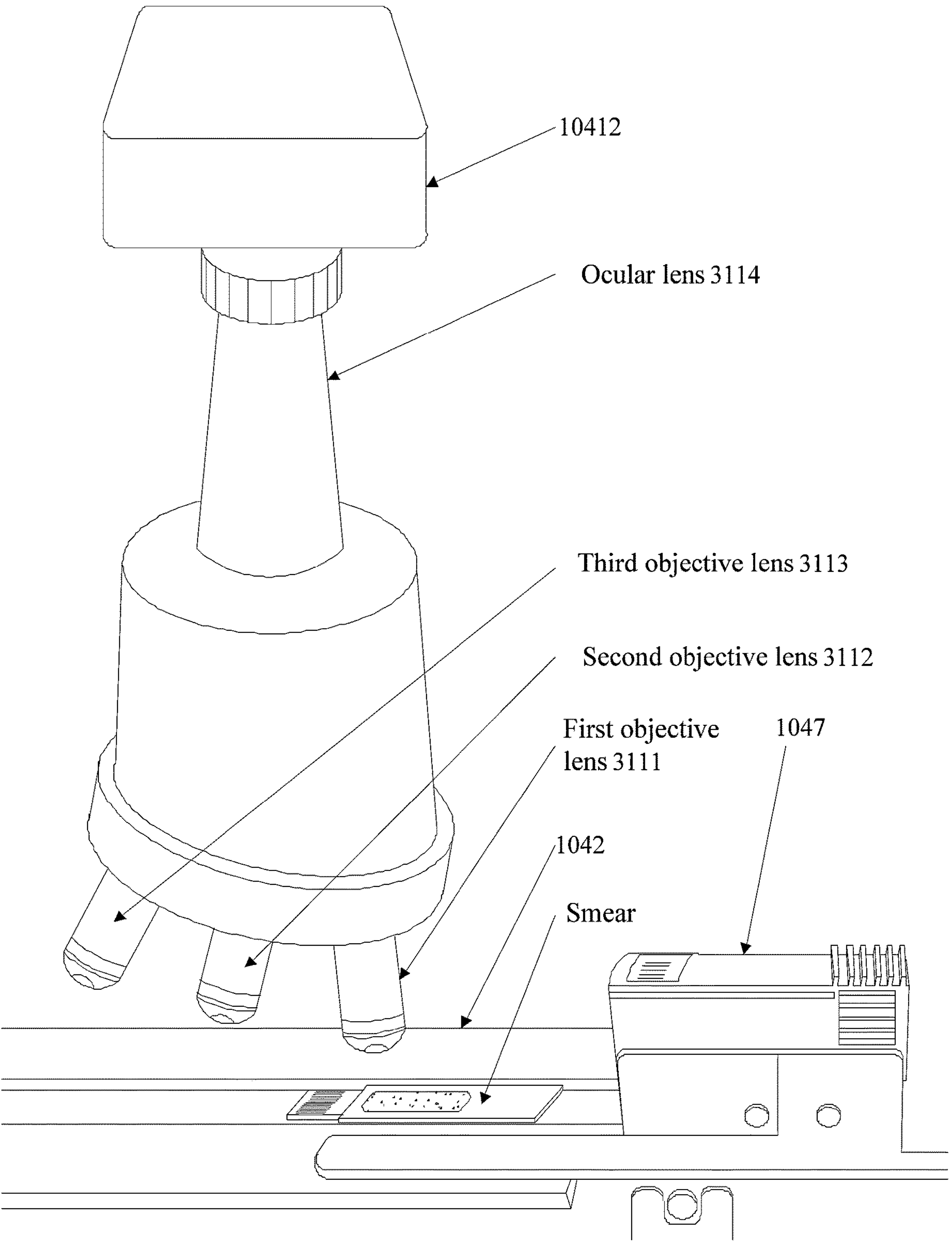

For the sample analysis system shown in FIG. 1, an optional structure of the cell image analysis apparatus in each sample analysis system is shown in FIGS. 4 and 5. The cell image analysis apparatus at least includes an imaging apparatus 1041, a smear moving apparatus 1042, and an image analysis apparatus 1043.

The imaging apparatus 1041 includes a camera 10412 and a lens group 10411 and is configured to image cells in a sample to be analyzed that is smeared on a smear. The smear moving apparatus 1042 is configured to move the smear relative to the imaging apparatus 1041, such that the imaging apparatus 1041 captures cell images in a specific region of the smear. The image analysis apparatus 1043 is configured to analyze the cell images of the smear.

As shown in FIG. 5, the lens group 10411 may include a first objective lens 3111, a second objective lens 3112, and an ocular lens 3114. One of the first objective lens 3111 and the second objective lens 3112 is a low-power objective lens, and the other is a high-power objective lens. For example, the first objective lens 3111 is a high-power objective lens, and the second objective lens 3112 is a low-power objective lens. For example, the first objective lens may be a 100× objective lens, and the second objective lens 3112 may be a 10× objective lens. The lens group 10411 may further include a third objective lens 3113. A power of the third objective lens 3113 is between the powers of the first objective lens and the second objective lens. For example, the third objective lens 3113 may be a 40× objective lens.

The cell image analysis apparatus 104 further includes an identification apparatus 1044, a smear gripping apparatus 1045, and a smear recycle apparatus 1046. The identification apparatus 1044 is configured to identify sample information of the smear. The smear gripping apparatus 1045 is configured to grip the smear from the identification apparatus 1044 to the smear moving apparatus 1042, so that the smear moving apparatus 1042 drives the smear to move relative to the imaging apparatus 1041. Further, after the imaging apparatus 1041 captures cell images of the smear, the image analysis apparatus 1043 analyzes the cell images of the smear. The smear recycle apparatus 1046 is configured for placing smears that have been analyzed by the image analysis apparatus 1043.

The cell image analysis apparatus 104 further includes a smear basket loading apparatus 1047 configured to load a smear basket containing smears to be tested. The smear gripping apparatus 1045 is further configured to grip a smear in the smear basket loaded on the smear basket loading apparatus 1047 to the identification apparatus 1044 for sample information identification.

In this embodiment, the smears in the smear basket loaded on the smear basket loading apparatus 1047 may be placed in the smear basket by a user, or may be transported by another transport apparatus, so that smears prepared by the smear preparation apparatus are transported by the transport apparatus to the cell image analysis apparatus.

Figure 6:
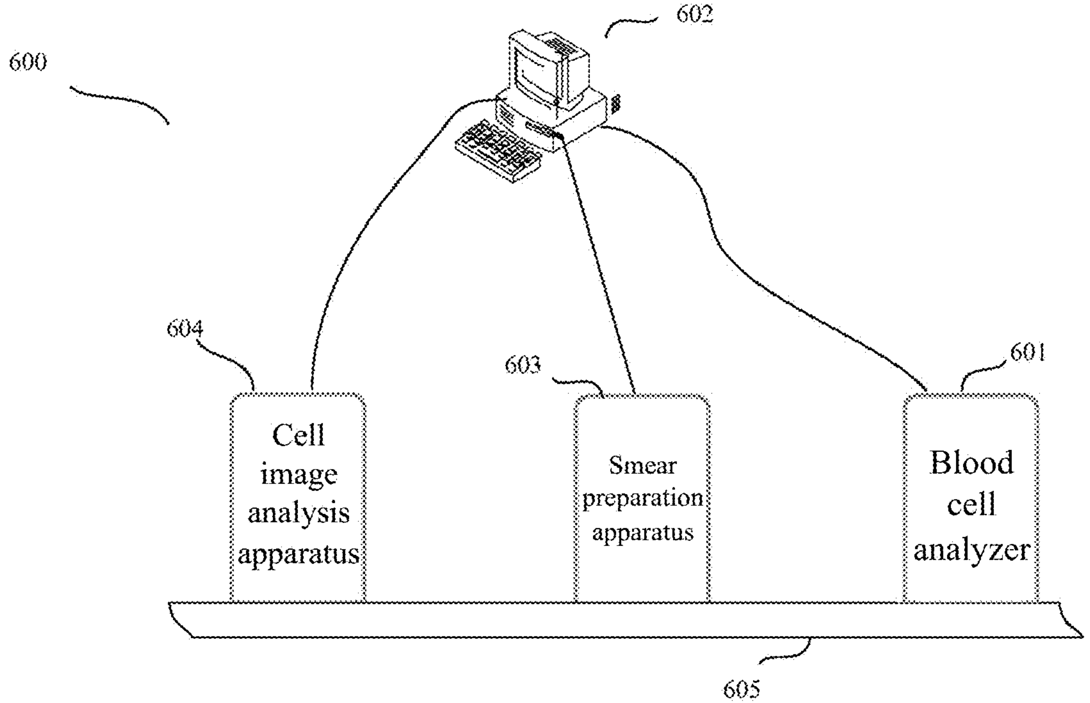
FIG. 6 is an schematic structural diagram of another sample analysis system according to an embodiment of the disclosure.

Based on this, this embodiment provides an optional structure of still another sample analysis system. As shown in FIG. 6, the sample analysis system 600 shown in FIG. 6 may include: a blood cell analyzer 601, a controller 602, a smear preparation apparatus 603, a cell image analysis apparatus 604, and a transport apparatus 605.

The transport apparatus 605 is configured to transport a sample to be analyzed from the blood cell analyzer 601 to the smear preparation apparatus 603, and to transport a smear from the smear preparation apparatus 603 to the cell image analysis apparatus 604, such that the transport apparatus 605 completes transportation of the sample to be analyzed between the blood cell analyzer 601, the smear preparation apparatus 603, and the cell image analysis apparatus 604. In this way, automated testing, smear preparation, and image capturing and analysis can be completed for any sample to be analyzed by the blood cell analyzer 601, the smear preparation apparatus 603, and the cell image analysis apparatus 604.

For the blood cell analyzer 601, the controller 602, the smear preparation apparatus 603, and the cell image analysis apparatus 604 of the sample analysis system 600 shown in FIG. 6, reference may be made to the description of the foregoing sample analysis system, and details are not described again in this embodiment.

Figure 7:
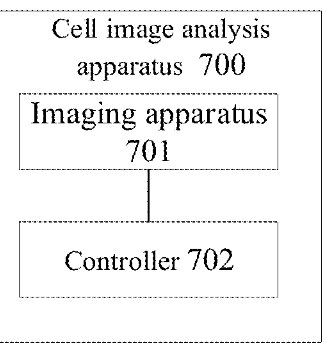
FIG. 7 is an schematic structural diagram of a cell image analysis apparatus according to an embodiment of the disclosure.

From the perspective of the sample analysis system, the foregoing describes that the controller in the sample analysis system selects the imaging condition. The cell image analysis apparatus may also select the imaging condition. FIG. 7 shows an optional structure of a cell image analysis apparatus. The cell image analysis apparatus 700 shown in FIG. 7 may include an imaging apparatus 701 and a controller 702.

The imaging apparatus 701 is configured to image a smear of a sample to be analyzed. For the structure of the imaging apparatus 701 in this embodiment, reference may be made to the imaging apparatus in the cell image analysis apparatus shown in FIGS. 4 and 5.

The controller 702 is configured to obtain a test result of the sample to be analyzed that is obtained by a blood cell analyzer through testing, and control the imaging apparatus 701 to select a corresponding analysis mode and/or imaging condition based on the test result, to capture and analyze cell images for the smear of the sample to be analyzed.

The controller 702 is further configured to: if a value of at least one type of cells in the test result of the sample to be analyzed is less than a preset threshold, control the imaging apparatus to image the smear of the sample to be analyzed under a first imaging condition, so as to obtain images of the at least one type of cells; if the value of the at least one type of cells in the test result of the sample to be analyzed is not less than the preset threshold, control the imaging apparatus to image the smear of the sample to be analyzed under a second imaging condition that is different from the first imaging condition, so as to obtain images of the at least one type of cells. The first imaging condition and the second imaging condition are different from each other in at least one of: number of cell images to be captured, imaging range, imaging position, power of an objective lens for imaging and focus range. For a structure of the controller 702 in this embodiment, reference may be made to the structure of the controller in the foregoing sample analysis system shown in FIG. 3. How the controller 702 selects a corresponding analysis mode and/or imaging condition based on the test result is similar to the foregoing embodiments, and details are not described herein again.

A difference from the foregoing sample analysis system lies in that: in this embodiment, the controller in the cell image analysis apparatus selects the imaging condition, and the controller in the cell image analysis apparatus selects the imaging condition based on a relationship between the value of the at least one type of cells in the test result of the sample to be analyzed and the preset threshold.

For example, if the value of the at least one type of cells in the test result of the sample to be analyzed is less than the preset threshold, the first imaging condition is to be selected; and if the value of the at least one type of cells in the test result of the sample to be analyzed is not less than the preset threshold, the second imaging condition is to be selected. The first imaging condition and the second imaging condition used are different from each other in at least one of: number of cell images to be captured, imaging range, imaging position, power of an objective lens for imaging and focus range. For details, reference may be made to the description of the controller in the foregoing sample analysis system.

In this embodiment, the value of the at least one type of cells includes at least one of a number, a proportion, and a volume of the at least one type of cells. For the description of the value of the at least one type of cells, reference may be made to the description in the sample analysis system shown in FIG. 1.

According to the cell image analysis apparatus shown in FIG. 7, the controller in the cell image analysis apparatus selects the imaging condition based on the relationship between the value of the at least one type of cells in the test result of the sample to be analyzed and the preset threshold, so that during analysis of any sample to be analyzed, the cell image analysis apparatus can select a matching imaging condition based on the test result of the sample to be analyzed, which facilitates selection of the imaging condition and improves processing efficiency and accuracy.

Figure 8:
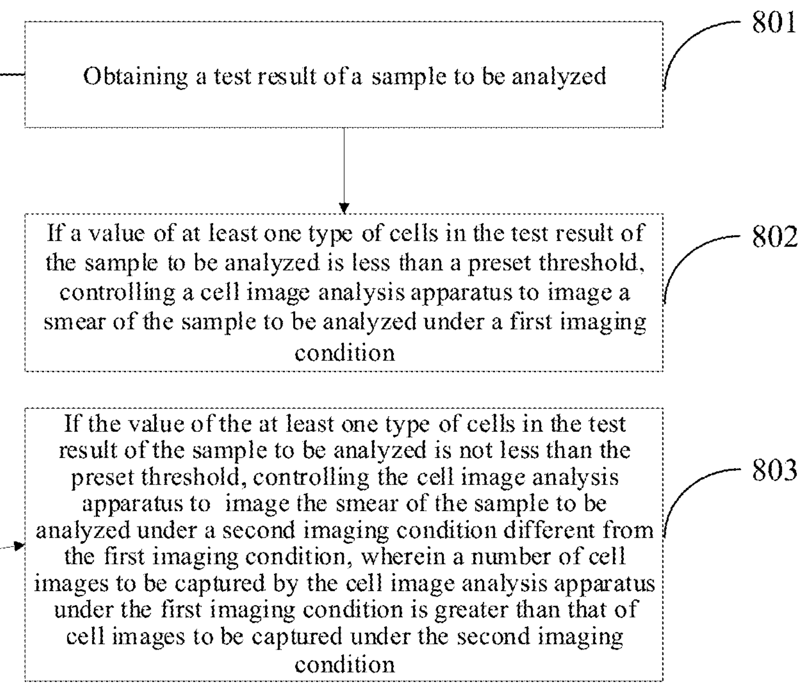
FIG. 8 is an flowchart of a blood cell analysis method according to an embodiment of the disclosure.

Referring to FIG. 8, FIG. 8 is an flowchart of a blood cell analysis method according to an embodiment of the disclosure. The blood cell analysis method shown in FIG. 8 corresponds to the foregoing sample analysis system shown in FIG. 1. For the description of the blood cell analysis method shown in FIG. 8, reference may be made to the sample analysis system shown in FIG. 1, and details are not described again in this embodiment. The blood cell analysis method shown in FIG. 8 may include the following steps:

801: obtaining a test result of a sample to be analyzed.

802: if a value of at least one type of cells in the test result of the sample to be analyzed is less than a preset threshold, controlling a cell image analysis apparatus to image a smear of the sample to be analyzed under a first imaging condition, so as to obtain images of the at least one type of cells.

803: if the value of the at least one type of cells in the test result of the sample to be analyzed is not less than the preset threshold, controlling the cell image analysis apparatus to image the smear of the sample to be analyzed under a second imaging condition that is different from the first imaging condition, so as to obtain images of the at least one type of cells.

A number of cell images to be captured by the cell image analysis apparatus under the first imaging condition is greater than that of cell images to be captured under the second imaging condition.

According to the blood cell analysis method shown in FIG. 8, a matching imaging condition can be selected based on a relationship between the value of the at least one type of cells in the test result of the sample to be analyzed and the preset threshold, so as to use the matching imaging condition to specifically capture and analyze the cell images of the sample to be analyzed (for example, an abnormal part indicated by the test result of the sample to be analyzed is specifically imaged), so that the cell image analysis apparatus can obtain and analyze cell images matching the test result, which improves processing efficiency and accuracy of the cell image analysis apparatus.

In this embodiment, the value of the at least one type of cells includes at least one of a number, a proportion and a volume of the at least one type of cells, or the value of the at least one type of cells includes at least one of a white blood cell count, a red blood cell count and a platelet count.

During the selection of the matching imaging condition based on the relationship between the value of the at least one type of cells in the test result of the sample to be analyzed and the preset threshold, the selected imaging condition may be the following: at least one of an imaging range and an imaging position corresponding to the first imaging condition is different from at least one of those corresponding to the second imaging condition. In other words, the first imaging condition and the second imaging condition are different from each other in at least one of the number of cell images, the imaging range and the imaging position.

For example, the imaging range of the cell image analysis apparatus for imaging the smear under the first imaging condition is larger than that for imaging the smear under the second imaging condition; and the imaging position of the cell image analysis apparatus for imaging the smear under the first imaging condition is different from that for imaging the smear under the second imaging condition.

In this embodiment, the at least one type of cells may include platelets. For platelets, when a relationship between a platelet count and a corresponding preset threshold is different, a corresponding imaging position is different. For example, if the platelet count in the test result of the sample to be analyzed is less than the corresponding preset threshold, the cell image analysis apparatus is controlled to use the first imaging condition; or if the platelet count in the test result of the sample to be analyzed is not less than the corresponding preset threshold, the cell image analysis apparatus is controlled to use the second imaging condition.

The imaging position of the cell image analysis apparatus for imaging the smear under the first imaging condition includes the tail portion and/or edge portion of the smear, and the imaging position for imaging the smear under the second imaging condition includes the body portion of the smear. The reason for imaging in this manner is as follows: if the platelet count is less than the preset threshold, platelet aggregation may be present in the sample to be analyzed, therefore, by imaging the tail portion and/or the edge portion to obtain cell images for the corresponding regions and then analyzing the cell images of the tail portion and/or the edge portion, it can be determined whether the decrease in the platelet count (i.e., less than the preset threshold) is caused by platelet aggregation.

Figure 9:
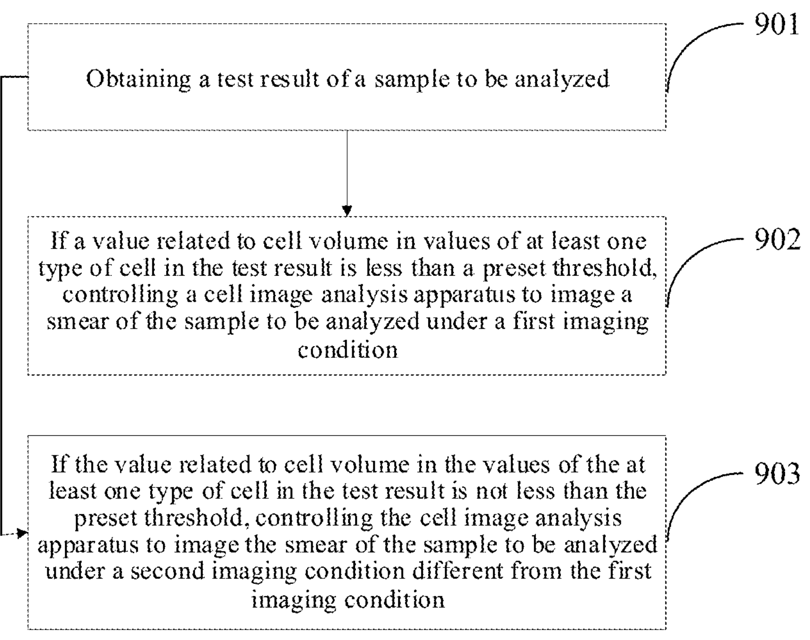
FIG. 9 is an flowchart of another blood cell analysis method according to an embodiment of the disclosure.

FIG. 9 shows an optional procedure of another blood cell analysis method according to an embodiment of the disclosure, and may include the following steps:

901: obtaining a test result of a sample to be analyzed.

902: if a value related to cell volume in values of at least one type of cells in the test result is less than a preset threshold, controlling a cell image analysis apparatus to image a smear of the sample to be analyzed under a first imaging condition, so as to obtain images of the at least one type of cells.

903: if the value related to cell volume in the values of the at least one type of cells in the test result is not less than the preset threshold, controlling the cell image analysis apparatus to image the smear of the sample to be analyzed under a second imaging condition that is different from the first imaging condition, so as to obtain images of the at least one type of cells.

The blood cell analysis method shown in FIG. 9 corresponds to the foregoing sample analysis system shown in FIG. 1. For the description of the blood cell analysis method shown in FIG. 9, reference may be made to the sample analysis system shown in FIG. 1, and details are not described again in this embodiment.

A focus range corresponding to the first imaging condition is different from that corresponding to the second imaging condition, and a difference between the focus ranges may be that the focus range corresponding to the second imaging condition is larger than that corresponding to the first imaging condition. For example, small cells (the value related to cell volume is less than the preset threshold) are imaged using a smaller focus range, and large cells (the value related to cell volume is greater than the preset threshold) are imaged using a larger focus range. Imaging with a larger focus range can ensure clarity of large cells, and imaging small cells with a smaller focus range can not only ensure clarity but also reduce imaging time.

The foregoing sample analysis system shown in FIG. 9 can select an imaging condition for the cell image analysis apparatus based on a relationship between the value related to cell volume and the preset threshold, and thereby select a matching imaging condition based on the value related to cell volume in the test result, so that the cell image analysis apparatus can obtain and analyze cell images matching the test result, which improves processing efficiency and accuracy of the cell image analysis apparatus.

Figure 10:
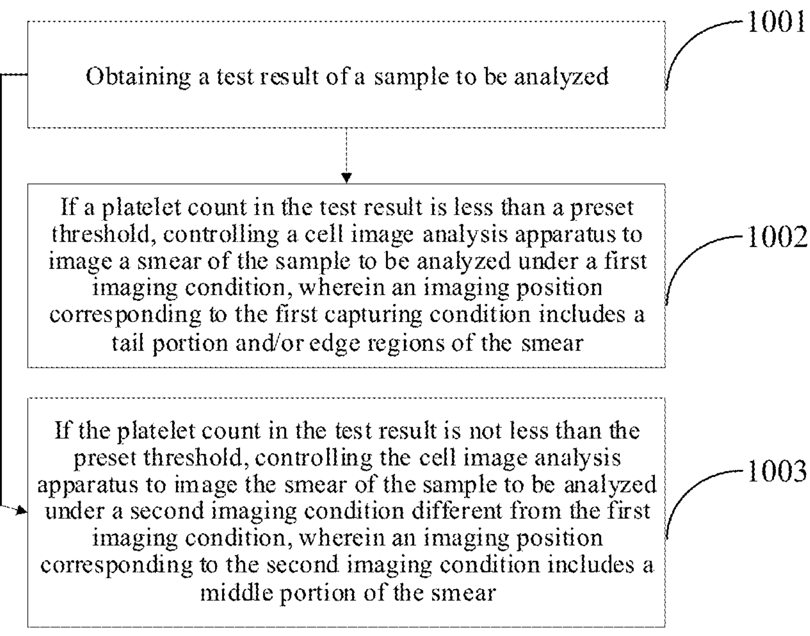
FIG. 10 is an flowchart of still another blood cell analysis method according to an embodiment of the disclosure.

FIG. 10 shows an optional procedure of still another blood cell analysis method according to an embodiment of the disclosure. The blood cell analysis method shown in FIG. 10 is directed to platelets, and selecting an imaging condition based on a relationship between a platelet count and a preset threshold may include the following steps:

1001: obtaining a test result of a sample to be analyzed.

1002: if a platelet count in the test result is less than a preset threshold, controlling a cell image analysis apparatus to image a smear of the sample to be analyzed under a first imaging condition, so as to obtain images of the at least one type of cells.

1003: if the platelet count in the test result is not less than the preset threshold, control the cell image analysis apparatus to image the smear of the sample to be analyzed under a second imaging condition that is different from the first imaging condition, so as to obtain images of the at least one type of cells.

An imaging position corresponding to the first imaging condition includes a tail portion and/or edge portion of the smear, and an imaging position corresponding to the second imaging condition includes a body portion of the smear.

For the description of the blood cell analysis method shown in FIG. 10, reference may be made to the foregoing sample analysis system. According to the blood cell analysis method shown in FIG. 10, the imaging condition may be selected based on the relationship between the platelet count and the preset threshold, and especially when the platelet count decreases (the platelet count is less than the preset threshold), the tail portion and/or edge portion of the smear are controlled to be imaged, to determine whether the decrease in the platelet count is caused by platelet aggregation. A cause for the decrease in the platelet count is determined by imaging the platelets in a targeted manner.

Figure 11:
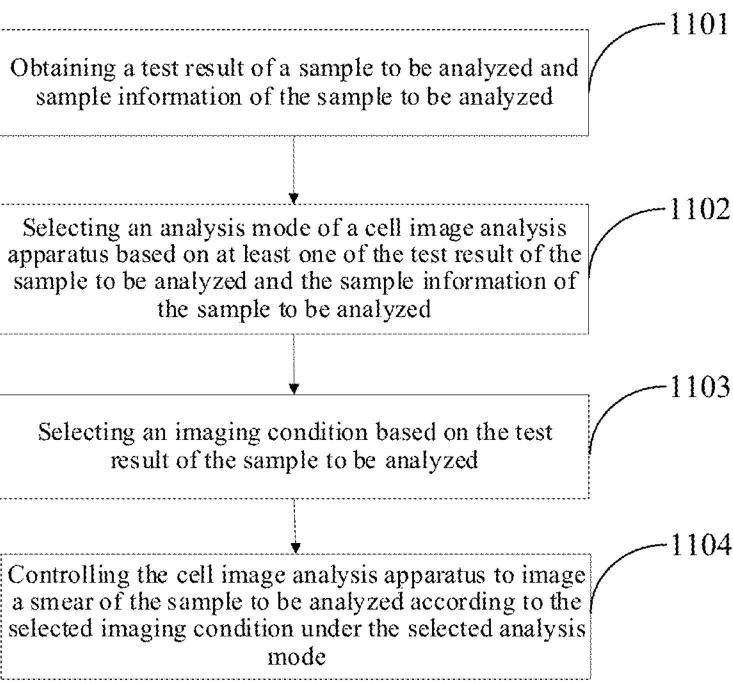
FIG. 11 is an flowchart of still another blood cell analysis method according to an embodiment of the disclosure.

Referring to FIG. 11, FIG. 11 shows an optional procedure of still another blood cell analysis method according to an embodiment of the disclosure. The blood cell analysis method shown in FIG. 11 corresponds to the foregoing sample analysis system shown in FIG. 1. For the description of the blood cell analysis method shown in FIG. 11, reference may be made to the sample analysis system shown in FIG. 1, and details are not described again in this embodiment. The blood cell analysis method shown in FIG. 11 may include the following steps:

1101: obtaining a test result of a sample to be analyzed and sample information of the sample to be analyzed.

1102: selecting an analysis mode of a cell image analysis apparatus based on at least one of the test result of the sample to be analyzed and the sample information of the sample to be analyzed, the analysis mode including at least one of a white blood cell analysis mode, a red blood cell analysis mode, a platelet analysis mode and a combination of at least two of aforesaid modes.

1103: selecting an imaging condition based on the test result of the sample to be analyzed.

1104: controlling the cell image analysis apparatus to image a smear of the sample to be analyzed according to the selected imaging condition under the selected analysis mode.

The imaging condition is related to at least one of a number of cell images to be captured, an imaging range, an imaging position, a power of an objective lens for imaging and a focus range.

Analysis modes and imaging conditions that match three types of cells, namely white blood cells, red blood cells, and platelets, are separately described below.

White Blood Cells

A method of selecting an analysis mode based on white blood cells in the test result may be as follows: selecting an analysis mode of a cell image analysis apparatus based on at least one of the test result of the sample to be analyzed and the sample information of the sample to be analyzed includes: if the test result of the sample to be analyzed includes abnormality information related to white blood cells, selecting the white blood cell analysis mode or a combination mode including the white blood cell analysis mode.

Correspondingly, a method of selecting an imaging condition based on white blood cells in the test result may be as follows: selecting an imaging condition based on the test result of the sample to be analyzed includes: selecting a first imaging condition if the abnormality information related to white blood cells indicates that a white blood cell count is lower than a first preset threshold or indicates presence of abnormal cells related to white blood cells; selecting a second imaging condition if the abnormality information related to white blood cells indicates that the white blood cell count is not lower than the first preset threshold or indicates that there are no abnormal cells related to white blood cells.

The number of white blood cell images to be captured corresponding to the first imaging condition is greater than that of white blood cell images to be captured corresponding to the second imaging condition.

Red Blood Cells

A method of selecting an analysis mode based on red blood cells in the test result may be as follows: selecting an analysis mode of a cell image analysis apparatus based on at least one of the test result of the sample to be analyzed and the sample information of the sample to be analyzed includes: if the test result of the sample to be analyzed includes abnormality information related to red blood cells, selecting the red blood cell analysis mode or a combination mode including the red blood cell analysis mode, the abnormality information related to red blood cells including, but not limited to, at least one of a red blood cell count deviating from a normal range, red blood cell aggregation, fragmented red blood cells, and a red blood cell volume being less than a preset volume.

Correspondingly, a method of selecting an imaging condition based on red blood cells in the test result may be as follows: selecting an imaging condition based on the test result of the sample to be analyzed includes: if the abnormality information related to red blood cells includes red blood cell aggregation, selecting an imaging condition indicating to image a tail portion of the smear; or if the red blood cell volume (MCV) is less than the preset volume, selecting an imaging condition indicating to scan red blood cells in a small area on the smear.

Platelets

A method of selecting an analysis mode based on platelets in the test result may be as follows: selecting an analysis mode of a cell image analysis apparatus based on at least one of the test result of the sample to be analyzed and the sample information of the sample to be analyzed includes: if the test result of the sample to be analyzed includes abnormality information related to platelets, selecting the platelet analysis mode or a combination mode including the platelet analysis mode, the abnormality information related to platelets including at least one of platelet aggregation and a platelet count being lower than a second preset threshold.

Correspondingly, a method of selecting an imaging condition based on platelets in the test result may be as follows: selecting an imaging condition based on the test result of the sample to be analyzed includes: selecting a first imaging condition if the platelet count is lower than the second preset threshold; selecting a second imaging condition if the platelet count is not lower than the second preset threshold, wherein an imaging position or imaging range corresponding to the first imaging condition is different from that corresponding to the second imaging condition.

For example, the imaging range corresponding to the first imaging condition is larger than that corresponding to the second imaging condition. Alternatively, the imaging position corresponding to the first imaging condition includes a tail portion and/or edge portion of the smear; and the imaging position corresponding to the second imaging condition includes a body portion of the smear.

Other methods of selecting an analysis mode and an imaging condition are as follows:

One method of selecting the analysis mode: selecting an analysis mode of a cell image analysis apparatus based on at least one of the test result of the sample to be analyzed and the sample information of the sample to be analyzed includes: selecting a combination mode of the white blood cell analysis mode, the red blood cell analysis mode and the platelet analysis mode if white blood cells, red blood cells and platelets in the test result of the sample to be analyzed are all lower than respective preset thresholds.

Another method of selecting the analysis mode: selecting a combination mode of the white blood cell analysis mode, the red blood cell analysis mode and the platelet analysis mode if the sample information includes information indicating that the sample to be analyzed is from a pediatric department and there is no historical medical record.

One method of selecting the imaging condition based on the test result may be: determining whether preset abnormality information is present based on the test result of the sample to be analyzed; and selecting a first imaging condition if a first type of abnormality information is present; selecting a second imaging condition that is different from the first imaging condition if a second type of abnormality information is present.

The first type of abnormality information includes abnormal cell prompt or alarm information, and the first imaging condition includes selecting a first objective lens to image the smear of the sample to be analyzed; and the second type of abnormality information includes information about a cell classification proportion abnormality, and the second imaging condition includes selecting a second objective lens to image the smear of the sample to be analyzed, wherein a power of the first objective lens is higher than that of the second objective lens;

or the first type of abnormality information includes a proportion of abnormal cells related to white blood cells being less than a preset proportion, the second type of abnormality information includes the proportion of abnormal cells related to white blood cells being not less than the preset proportion, and the number of white blood cell images to be captured corresponding to the first imaging condition is less than that of white blood cell images to be captured corresponding to the second imaging condition.

Another method of selecting the imaging condition based on the test result of the sample to be analyzed: if the selected analysis mode is the white blood cell analysis mode or a combination mode including the white blood cell analysis mode, determining whether the number of red blood cells is less than a preset threshold based on the test result.

If the number of red blood cells is less than the preset threshold, the first imaging condition is selected to capture white blood cell images; and if the number of red blood cells is not less than the preset threshold, the second imaging condition that is different from the first imaging condition is selected to capture white blood cell images.

The first imaging condition and the second imaging condition are different from each other in imaging position.

According to the blood cell analysis method shown in FIG. 11, a matching analysis mode is selected based on at least one of the test result and the sample information, and a matching imaging condition is selected based on the test result, which achieves automatic selection of the analysis mode and the imaging condition, and improves processing efficiency of the cell image analysis apparatus. In addition, the cell image analysis apparatus can work under the analysis mode and the imaging condition matching the sample to be analyzed, which improves processing efficiency and accuracy of the cell image analysis apparatus.

Figure 12:
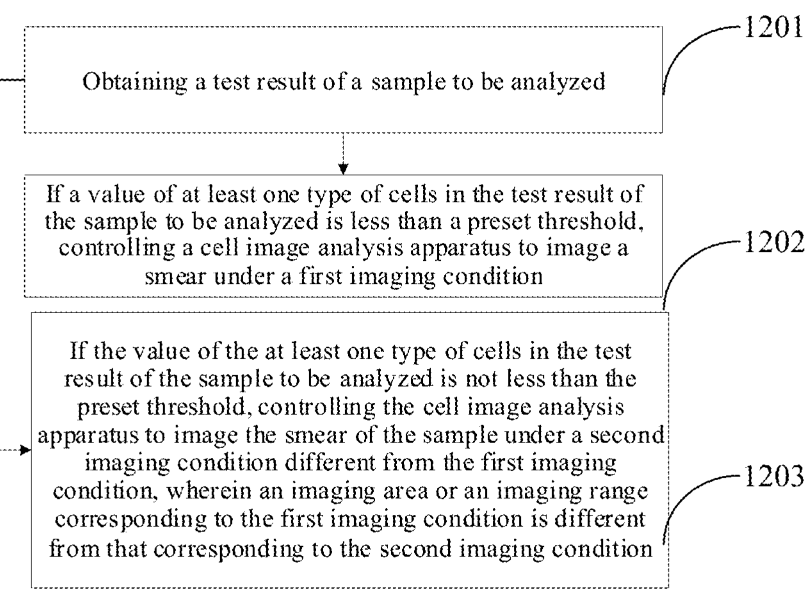
FIG. 12 is an flowchart of still another blood cell analysis method according to an embodiment of the disclosure.

FIG. 12 shows an optional procedure of still another blood cell analysis method according to an embodiment of the disclosure. The blood cell analysis method shown in FIG. 12 corresponds to the foregoing sample analysis system shown in FIG. 1. For the description of the blood cell analysis method shown in FIG. 12, reference may be made to the sample analysis system shown in FIG. 1, and details are not described again in this embodiment. The blood cell analysis method shown in FIG. 12 may include the following steps:

1201: obtaining a test result of a sample to be analyzed.

1202: if a value of at least one type of cells in the test result of the sample to be analyzed is less than a preset threshold, controlling a cell image analysis apparatus to image a smear under a first imaging condition, so as to obtain images of the at least one type of cells.

1203: if the value of the at least one type of cells in the test result of the sample to be analyzed is not less than the preset threshold, controlling the cell image analysis apparatus to image the smear of the sample under a second imaging condition that is different from the first imaging condition, so as to obtain images of the at least one type of cells.

The first imaging condition and the second imaging condition are different from each other in imaging range. For example, the imaging range corresponding to the first imaging condition is larger than that corresponding to the second imaging condition. In this embodiment, the value of the at least one type of cells includes, but is not limited to, the number of white blood cells, the number of red blood cells, or the number of platelets.

According to the blood cell analysis method shown in FIG. 12, the imaging range of the cell image analysis apparatus is controlled based on a relationship between the value of the at least one type of cells in the test result and the preset threshold, such that the imaging range is different in different situations.

An embodiment of the disclosure further provides still another blood cell analysis method, including the following steps:

(1) Obtaining a test result of a sample to be analyzed.

(2) If the test result of the sample to be analyzed indicates presence of abnormal cells, adjusting a number of cell images to be captured based on a proportion of abnormal cells. The higher the proportion of abnormal cells, the larger the number of cell images to be captured by the cell image analysis apparatus. For example, if the test result of the sample to be analyzed indicates presence of NRBCs, the higher the proportion of NRBCs, the larger the number of cell (e.g., white blood cell) images to be captured by the cell image analysis apparatus 104. For example, if the proportion of NRBCs is 1%, the cell image analysis apparatus 104 captures 150 white blood cell images; and if the proportion of NRBCs is 2%, the cell image analysis apparatus 104 captures 200 white blood cell images. For detailed description, reference may be made to the foregoing system embodiments, and details are not described again in this embodiment.

Figure 13:
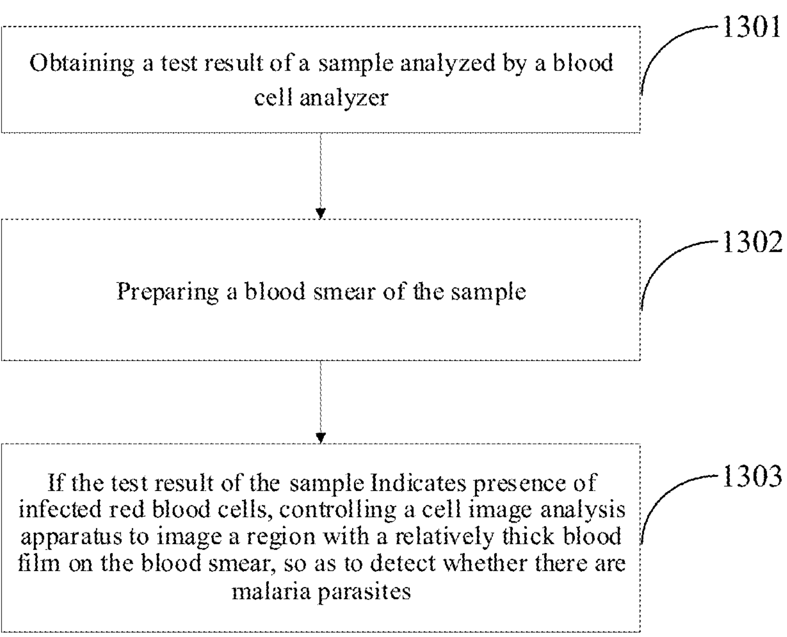
FIG. 13 is an flowchart of still another blood cell analysis method according to an embodiment of the disclosure.

As shown in FIG. 13, in still another embodiment of the disclosure, a blood cell analysis method includes the following steps:

1301: obtaining a test result of a sample analyzed by a blood cell analyzer.

1302: preparing a blood smear of the sample. A process of preparing a blood smear includes aspirating the sample to be analyzed, dropping the sample onto a slide, smearing the sample on the slide into a blood film to prepare a blood smear, and then staining and drying the blood smear, to complete the preparation of the blood smear of the sample.

1303: if the test result of the sample indicates presence of infected red blood cells, controlling a cell image analysis apparatus to image a region with a relatively thick blood film on the blood smear, so as to detect whether there are malaria parasites, wherein the region with the relatively thick blood film on the blood smear includes a body portion and a tail portion of the blood smear. The thickness of the blood film on the blood smear gradually decreases from the head portion to the body portion, and from the body portion to the tail portion, that is, the thickness of the blood film in the head portion and body portion is greater than that in the tail portion. In the region with a relatively thick blood film, it is easier to find malaria parasites. Therefore, in the case of an alarm of infected red blood cells, it is easier to observe malaria parasites on the body portion or head portion of the blood smear, thereby improving test efficiency.

An embodiment of the disclosure further provides a storage medium storing executable instructions, which is configured to cause a processor to execute the executable instructions to implement one of the foregoing blood cell analysis methods.

Those skilled in the art should understand that the embodiments of the disclosure may be provided as a method, a system, or a computer program product. Therefore, the embodiments of the disclosure may take the form of hardware embodiments, software embodiments, or embodiments with a combination of software and hardware. Moreover, the embodiments of the disclosure may take the form of a computer program product that is implemented on one or more computer-usable storage media (including a disk memory and an optical memory, etc.) that include computer-usable program code.

The embodiments of the disclosure are described with reference to flowcharts and/or block diagrams of the methods, devices (systems), and computer program products according to the embodiments of the disclosure. It should be understood that each procedure and/or block in the flowcharts and/or block diagrams, and combinations of the procedures and/or blocks in the flowcharts and/or block diagrams may be implemented by computer program operations. These computer program operations may be provided to a processor of a general-purpose computer, a special-purpose computer, an embedded processor, or another programmable data processing device to generate a machine, such that the operations executed by the processor of the computer or another programmable data processing device generate an apparatus for implementing a specific function in one or more procedures in the flowcharts and/or one or more blocks in the block diagrams.

These computer program operations may be stored in a computer-readable memory that can direct the computer or another programmable data processing device to work in a specific manner, such that the operations stored in the computer-readable memory generate an artifact that includes an operation apparatus. The operation apparatus implements a specific function in one or more procedures in the flowcharts and/or in one or more blocks in the block diagrams.

These computer program operations may also be loaded onto the computer or another programmable data processing device, such that a series of operations and steps are performed on the computer or another programmable device, thereby generating computer-implemented processing. Therefore, the operations executed on the computer or another programmable device provide steps for implementing a specific function in one or more procedures in the flowcharts and/or in one or more blocks in the block diagrams.

The above description is only the preferred embodiments of the disclosure and is not intended to limit the scope of protection of the disclosure. Any modifications, equivalent substitutions, improvements, etc. made within the spirit and principles of the disclosure shall fall within the scope of protection of the disclosure.

What is claimed is:

1. A sample analysis system, comprising:

a blood cell analyzer configured to test at least one sample to obtain a test result of the at least one sample, wherein the at least one sample is a blood sample or a body fluid sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to:

if a value of at least one type of cells in the test result of the sample to be analyzed is less than a preset threshold, control the cell image analysis apparatus to image the smear of the sample to be analyzed under a first imaging condition, so as to obtain images of the at least one type of cells;

if the value of the at least one type of cells in the test result of the sample to be analyzed is not less than the preset threshold, control the cell image analysis apparatus to image the smear of the sample to be analyzed under a second imaging condition that is different from the first imaging condition, so as to obtain images of the at least one type of cells;

wherein a number of cell images to be captured by the cell image analysis apparatus under the first imaging condition is greater than that of cell images to be captured under the second imaging condition;

wherein the at least one type of cells comprises platelets, and the controller is further configured to:

control the cell image analysis apparatus to use the first imaging condition, if a platelet count in the test result of the sample to be analyzed is less than a corresponding preset threshold; or control the cell image analysis apparatus to use the second imaging condition, if the platelet count in the test result of the sample to be analyzed is not less than the corresponding preset threshold;

wherein an imaging position of the cell image analysis apparatus for imaging the smear under the first imaging condition comprises a tail portion and/or an edge portion of the smear; and an imaging position for imaging the smear under the second imaging condition comprises a body portion of the smear.

2. The sample analysis system of claim 1, wherein the value of the at least one type of cells comprises at least one of: a count value, a volume, or a proportion of the at least one type of cells.

3. The sample analysis system of claim 1, wherein the first imaging condition and the second imaging condition are different from each other in at least one of imaging range size and imaging position.

4. The sample analysis system of claim 1, wherein the value of the at least one type of cells comprises at least one of a white blood cell count, a red blood cell count, and a platelet count.

5. The sample analysis system of claim 1, wherein an imaging range of the cell image analysis apparatus for imaging the smear under the first imaging condition is larger than that for imaging the smear under the second imaging condition; and/or wherein an imaging position of the cell image analysis apparatus for imaging the smear under the first imaging condition is different from that for imaging the smear under the second imaging condition.

6. A sample analysis system, comprising:

a blood cell analyzer configured to test at least one sample to obtain a test result of the at least one sample, wherein the at least one sample is a blood sample or a body fluid sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images; wherein the controller is further configured to:

select an analysis mode of the cell image analysis apparatus based on at least one of the test result and sample information of the sample to be analyzed, wherein the analysis mode comprises at least one of a white blood cell analysis mode, a red blood cell analysis mode, and a platelet analysis mode, or a combination of at least two of aforesaid modes;

after selecting the analysis mode, select an imaging condition based on the test result of the sample to be analyzed; and control the cell image analysis apparatus to image the smear of the sample to be analyzed according to the selected imaging condition under the selected analysis mode;

wherein the controller is configured to:

if the test result of the sample to be analyzed comprises abnormality information related to platelets, select the platelet analysis mode or a combination mode comprising the platelet analysis mode, wherein the abnormality information related to platelets comprises at least one of platelet aggregation and a platelet count being lower than a second preset threshold; and the controller is further configured to:

select a first imaging condition if the platelet count is lower than the second preset threshold;

select a second imaging condition if the platelet count is not lower than the second preset threshold, wherein the first imaging condition and the second imaging condition are different from each other in imaging position or imaging range.

7. The sample analysis system of claim 6, wherein the imaging condition is related to at least one of: a number of cell images to be captured, an imaging range, an imaging position, a power of an objective lens for imaging, and a focus range.

8. The sample analysis system of claim 6, wherein the controller is further configured to select the imaging condition based on a value of at least one type of cells in the test result of the sample to be analyzed, wherein the value of the at least one type of cells comprises at least one of a number, a volume or a proportion of the type of cells.

9. The sample analysis system of claim 6, wherein the controller is configured to:

if the test result of the sample to be analyzed comprises abnormality information related to white blood cells, select the white blood cell analysis mode or a combination mode comprising the white blood cell analysis mode; and the controller is further configured to:

select a first imaging condition if the abnormality information related to white blood cells includes that a white blood cell count is lower than a first preset threshold or that abnormal cells related to white blood cells are present;

select a second imaging condition if the white blood cell count in the sample to be analyzed is not lower than the first preset threshold and there are no abnormal cells related to white blood cells;

wherein a number of white blood cell images to be captured corresponding to the first imaging condition is greater than that of white blood cell images to be captured corresponding to the second imaging condition.

10. The sample analysis system of claim 6, wherein the controller is configured to:

if the test result of the sample to be analyzed comprises abnormality information related to red blood cells, select the red blood cell analysis mode or a combination mode comprising the red blood cell analysis mode, wherein the abnormality information related to red blood cells comprises at least one of red blood cell aggregation, fragmented red blood cells, and a red blood cell volume being less than a preset volume.

11. The sample analysis system of claim 10, wherein the controller is further configured to:

control the cell image analysis apparatus to image a tail portion of the smear, if the abnormality information related to red blood cells comprises red blood cell aggregation.

12. The sample analysis system of claim 10, wherein the controller is configured to:

control the cell image analysis apparatus to image red blood cells in a small area on the smear, if the red blood cell volume is less than the preset volume.

13. The sample analysis system of claim 6, wherein the imaging range corresponding to the first imaging condition is larger than that corresponding to the second imaging condition; or the imaging position corresponding to the first imaging condition comprises a tail portion and/or an edge portion of the smear; and the imaging position corresponding to the second imaging condition comprises a body portion of the smear.

14. The sample analysis system of claim 6, wherein the controller is further configured to:

select a combination mode of the white blood cell analysis mode, the red blood cell analysis mode and the platelet analysis mode, if a white blood cell count, a hemoglobin concentration, and a platelet count in the test result of the sample to be analyzed are all lower than respective preset thresholds; or wherein the controller is configured to: select the analysis mode based on the sample information; and selecting the analysis mode based on the sample information comprises: select a combination mode of the white blood cell analysis mode, the red blood cell analysis mode and the platelet analysis mode, if the sample information indicates that the sample to be analyzed is from a pediatric department and there is no historical medical record.

15. A sample analysis system, comprising:

a blood cell analyzer configured to test at least one sample to obtain a test result of the at least one sample, wherein the at least one sample is a blood sample or a body fluid sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images; wherein the controller is further configured to:

select an analysis mode of the cell image analysis apparatus based on at least one of the test result and sample information of the sample to be analyzed, wherein the analysis mode comprises at least one of a white blood cell analysis mode, a red blood cell analysis mode, and a platelet analysis mode, or a combination of at least two of aforesaid modes;

after selecting the analysis mode, select an imaging condition based on the test result of the sample to be analyzed; and control the cell image analysis apparatus to image the smear of the sample to be analyzed according to the selected imaging condition under the selected analysis mode;

wherein the controller is configured to:

determine whether preset abnormality information is present in the test result of the sample to be analyzed; and select a first imaging condition if a first type of abnormality information is present; or select a second imaging condition different from the first imaging condition if a second type of abnormality information is present;

wherein the first type of abnormality information comprises abnormal cell prompt or alarm information for indicating the presence of abnormal cells, and the first imaging condition comprises selecting a first objective lens to image the smear of the sample to be analyzed; the second type of abnormality information comprises information about a cell classification proportion abnormality, and the second imaging condition comprises selecting a second objective lens to image the smear of the sample to be analyzed, wherein a power of the first objective lens is higher than that of the second objective lens; or, wherein the first type of abnormality information includes that a proportion of abnormal cells is less than a preset proportion, the second type of abnormality information includes that a proportion of abnormal cells is not less than a preset proportion, and a number of white blood cell images to be captured corresponding to the first imaging condition is less than that of white blood cell images to be captured corresponding to the second imaging condition.

16. A sample analysis system, comprising:

a blood cell analyzer configured to test at least one sample to obtain a test result of the at least one sample, wherein the at least one sample is a blood sample or a body fluid sample;

a controller configured to obtain the test result of the at least one sample;

a smear preparation apparatus configured to prepare a smear for a sample to be analyzed by a cell image analysis apparatus, so as to obtain the smear of the sample to be analyzed; and the cell image analysis apparatus configured to image and analyze the smear of the sample to be analyzed, so as to obtain cell images of the sample to be analyzed and an analysis result of the cell images;

wherein the controller is further configured to: if the test result of the sample to be analyzed indicates presence of abnormal cells, adjust a number of cells to be located and imaged based on a proportion of the abnormal cells;

wherein the abnormal cells comprise nucleated red blood cells; and adjusting a number of cells to be located and imaged based on a proportion of the abnormal cells comprises adjusting a number of white blood cells to be located and imaged based on a proportion of the nucleated red blood cells, wherein the higher the proportion of the nucleated red blood cells, the larger the number of white blood cells to be located; or, wherein the abnormal cells comprise blast cells; and adjusting a number of cells to be located and imaged based on a proportion of abnormal cells comprises adjusting a number of cells to be located and imaged based on a proportion of the blast cells, wherein the higher the proportion of the blast cells, the smaller the number of cells to be located and imaged; and the lower the proportion of blast cells, the larger the number of cells to be located and imaged.

* * * * *